United States Patent
Williams et al.

(10) Patent No.: US 11,318,293 B2
(45) Date of Patent: May 3, 2022

(54) SINGLE OR MULTI-DOSE DELIVERY PLATFORM FOR VETERINARY APPLICATIONS

(71) Applicant: Massachusetts Institute of Technology, Cambridge, MA (US)

(72) Inventors: Michael S. Williams, Enterprise, OR (US); Jason Siu Wei Li, Cambridge, MA (US); Jacob Coffey, Boston, MA (US); Christoph Winfried Johannes Steiger, Oberasbach (DE); Miguel Jimenez, Boston, MA (US); Robert S. Langer, Newton, MA (US); Ester Caffarel Salvador, Cambridge, MA (US); Alex Abramson, St. Louis, MO (US); Carlo Giovanni Traverso, Newton, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 128 days.

(21) Appl. No.: 16/696,233

(22) Filed: Nov. 26, 2019

(65) Prior Publication Data
US 2020/0164193 A1    May 28, 2020

Related U.S. Application Data

(60) Provisional application No. 62/771,324, filed on Nov. 26, 2018.

(51) Int. Cl.
*A61M 37/00*    (2006.01)
*A01K 11/00*    (2006.01)

(52) U.S. Cl.
CPC ....... *A61M 37/0015* (2013.01); *A01K 11/001* (2013.01); *A61M 2037/0023* (2013.01);
(Continued)

(58) Field of Classification Search
CPC ...... A61M 37/0015; A61M 2037/0023; A61M 2037/0061; A61M 2202/30; A61M 2250/00; A01K 11/001; A01K 11/003
See application file for complete search history.

(56) References Cited

U.S. PATENT DOCUMENTS

| 4,059,074 A | 11/1977 | Furer |
| 4,206,757 A | 6/1980 | Benet |

(Continued)

FOREIGN PATENT DOCUMENTS

WO    2009127542    10/2009

OTHER PUBLICATIONS

Merriam-Webster Dictionary definition for component, available online Dec. 2, 2021 at https://www.merriam-webster.com/dictionary/component. (Year: 2021).*

(Continued)

*Primary Examiner* — Amber R Stiles
(74) *Attorney, Agent, or Firm* — Pabst Patent Group LLP

(57) ABSTRACT

A platform technology has been designed to provide a means for controlled delivery of single or multiple doses of therapeutic, prophylactic, diagnostic or identifying agents to livestock. The delivery system is based on a livestock ear tag that releases therapeutic and/or prophylactic agent when applied to the ear or other desired anatomical target of the animal. The agent to be delivered is encapsulated in or on microneedles and or microparticles and or nanoparticles or combination thereof on a surface thereon of the male or female part of the tag, which is pressed into the skin so that the microneedles penetrate into the epidermis and dermis layers of the skin. The agent is then released into the animal from the microneedles and or microparticles and or nanoparticles or combination thereof at the site of contact into the epidermis and dermis layers of the skin.

21 Claims, 22 Drawing Sheets

(52) U.S. Cl.
    CPC . *A61M 2037/0061* (2013.01); *A61M 2202/30* (2013.01); *A61M 2250/00* (2013.01)

(56) References Cited

U.S. PATENT DOCUMENTS

| | | | | |
|---|---|---|---|---|
| 4,581,834 | A * | 4/1986 | Zatkos | A01K 11/001 119/655 |
| 5,189,986 | A | 3/1993 | Burkoth | |
| 5,782,799 | A | 7/1998 | Jacobsen | |
| 2010/0325926 | A1* | 12/2010 | Hilpert | A01K 11/001 40/301 |
| 2013/0190794 | A1* | 7/2013 | Kendall | A61B 5/14503 606/186 |
| 2016/0120628 | A1* | 5/2016 | Kapil | A61D 7/00 604/173 |
| 2016/0279401 | A1* | 9/2016 | Schwab | A61M 37/0015 |

OTHER PUBLICATIONS

Nejad, et al., "Three dimensional printing of metamaterial embedded geometrical optics (MEGO)", Microsystems & Nanoengineering, 4:17073 (2019).
Park, et al., "Biodegradable Polymer Microneedles: Fabrication, mechanics and Transdermal Drug Delivery", Journal of Controlled Release, 104 (1): 51-66 (2005).
International Search Report for corresponding PCT application PCT/US2019/063318 dated Mar. 6, 2020.

* cited by examiner

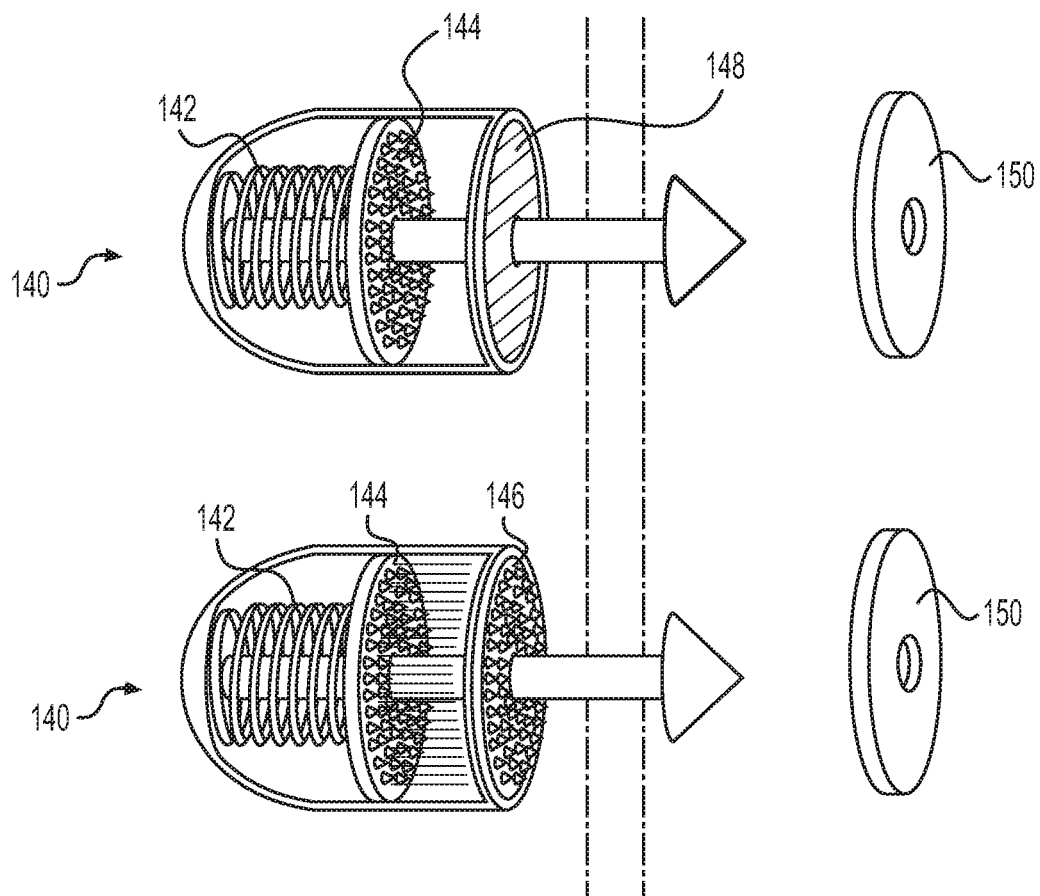
*FIG. 9A*          *FIG. 9B*

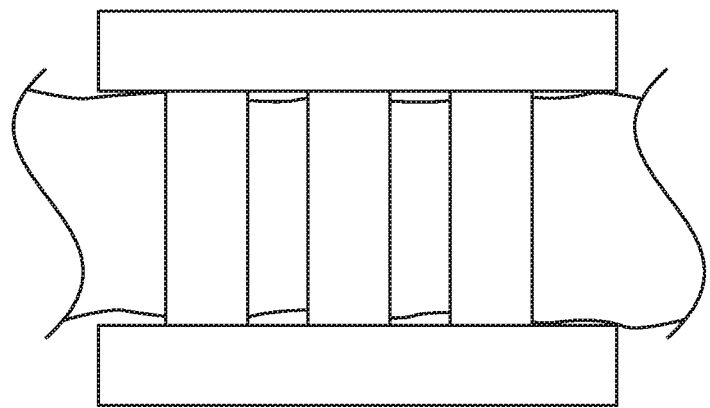
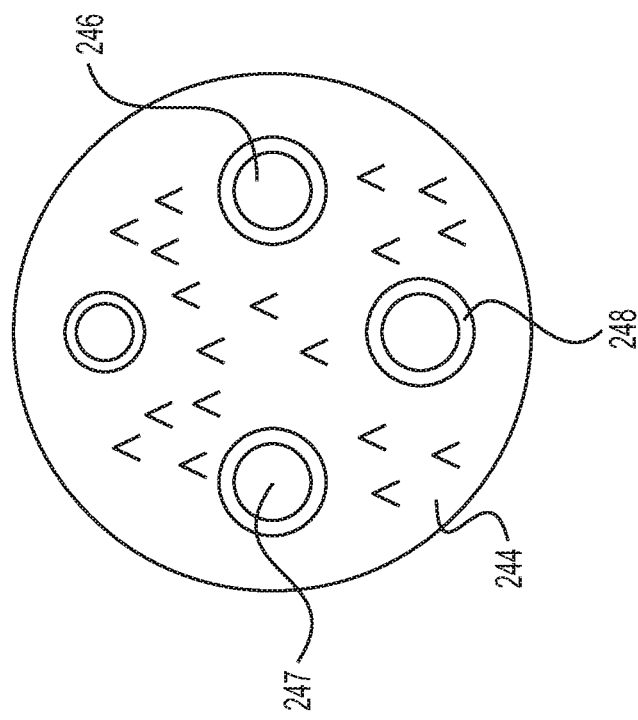
FIG. 16

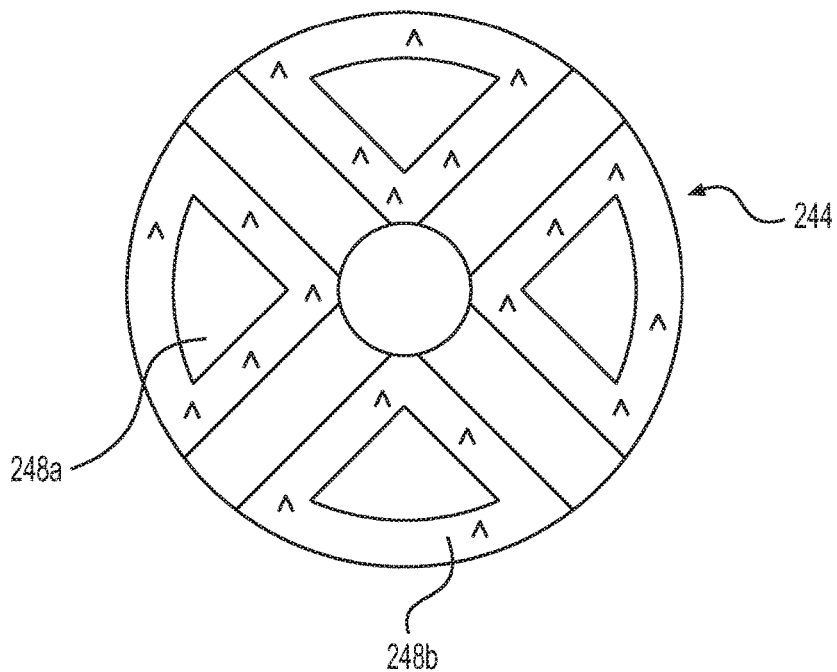
FIG. 17A
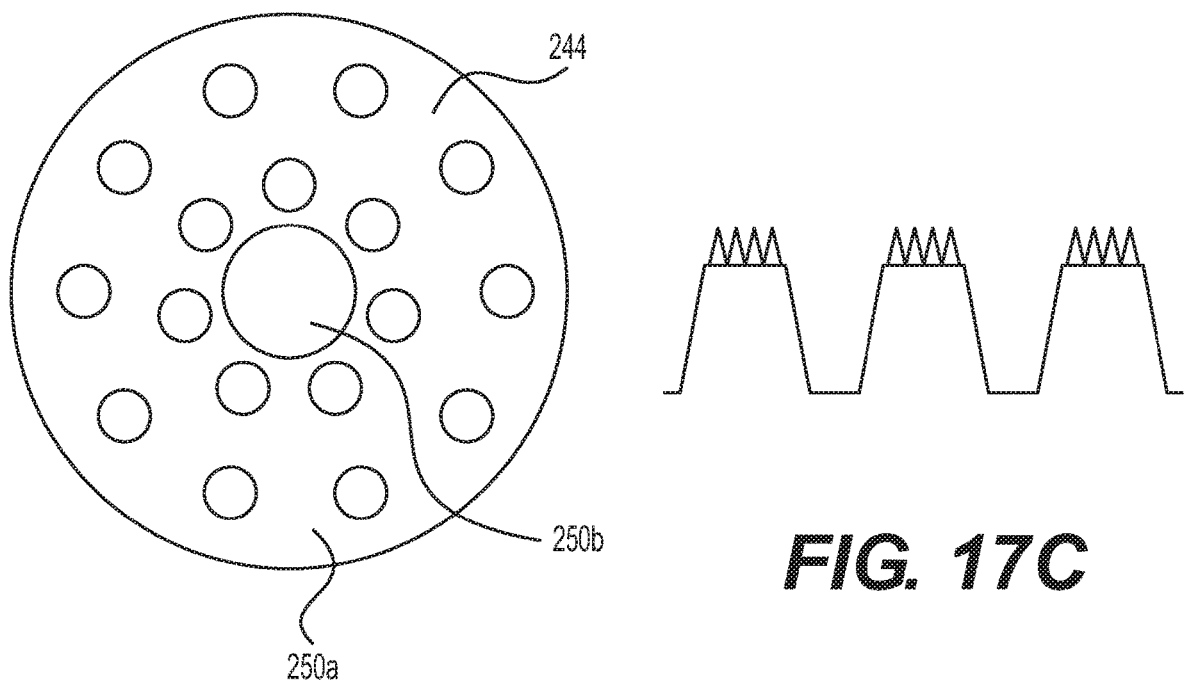
FIG. 17B
FIG. 17C

SINGLE OR MULTI-DOSE DELIVERY PLATFORM FOR VETERINARY APPLICATIONS

CROSS REFERENCE TO RELATED APPLICATION(S)

Priority is claimed to U.S. Ser. No. 62/771,324 filed on Nov. 26, 2018, the teachings of which are incorporated herein.

STATEMENT REGARDING FEDERALLY FUNDED RESEARCH

This invention was made with government support under NIH grant number RO1 EB000244 awarded by National Institutes of Health. The U.S. government has certain rights in this invention.

FIELD OF THE INVENTION

The present invention is in the field of drug delivery to animals, and more particularly in the area of ear tags or microneedle devices for administration of therapeutic, prophylactic and identification to animals, especially livestock.

BACKGROUND OF THE INVENTION

The current practice of vaccine delivery to livestock has inherent clinical and operational limitations. These limitations can negatively impact animal health, operational expense and production yields. Limitations include the inflexibility of management logistics around vaccination scheduling, repeated high-stress interventions which are directly related to health complications and the variability between actual and prescribed dosing protocols which can result in under immuno-protected (or immune-compromised) animals. As the demand for high quality, affordable and nutritious food keeps pace with the increase in the world's population, the need for a simple, intuitive, and reliable therapeutic delivery system that is better than traditional methods is greatly needed. In order to provide protective immunity, compliance with prescribed dosing protocols must be followed. Providing protective immunity reduces sickness, which in turn reduces the need for antibiotic administration, thereby reducing the escalation of antibiotic resistance.

Traditional delivery methods, by their nature, require multiple discreet and independent administrations. Adherence and compliance to prescribed administration protocols is often not achieved, primarily due to logistical and in many cases, financial reasons. It is therefore highly desirable to provide a mechanism by which to deliver vaccines with a single administration that provides a primary dose followed by additional booster doses in a highly tuned and controllable manner. Doing so will improve health through prescribed immunization compliance, growth performance and operational efficiency.

For example, conventional methods of veterinary vaccine administration in bovine calves involves two or more discrete hypodermic needle-based interventions, each a highly stressful event. Both killed and modified (attenuated) live vaccines are commonly used. Delays in booster administration, which are common due to logistics around grass cycles, can leave calves under-immunized during a critical phase of their lives when their natural immune system is not fully developed. Under-immunized animals are more likely to contract disease, spread disease, under-perform and in the case of zoonotic diseases, transmit dangerous pathogens to humans.

In order to achieve this objective, there are several challenges which must be resolved. The first is to eliminate the need for traditional needle injections which cause stress to animals, can transmit pathogens between animals and pose safety risks to both animals and applicators. Microneedle technology is one method by which to deliver vaccines, therapeutics and health-enhancing molecules while simultaneously addressing these issues of concern. A second challenge is to create a mechanism to load or coat stable and viable therapeutic concentrations of multiple active pharmaceutical ingredients (API's), adjuvant(s) and excipient(s) into or onto the microneedle delivery system. The solution to this challenge involves identifying and if necessary, optimizing and or enhancing the vaccine and the substrate to achieve suitable release profiles as well as material and biological compatibility.

Conventional methods of veterinary administration of therapeutic or prophylactic agents are typically by syringe and needle, most commonly with the animal restrained or, in rare cases using a remote access device such as a gun to fire vaccine or drug loaded syringe darts at a distant animal. In contrast to people, livestock such as sheep and goats, cattle and pigs, as well as exotic animals such as deer, antelope and other ungulates and equines, are often not cooperative in being caught or handled for repeat administration of therapeutic agents such as antibiotics and vaccines. This makes it particularly difficult to provide timely administrative of multiple treatments. Costs associated with repeated capture and handling are high, as are the costs to the animals due to stress and risk of injury during capture and treatment. Even in the situation where the patient is a young animal such as a calf or lamb, the mother can represent a significant threat to the party who is to treat the animal, and may prevent capture or restraint.

A number of alternatives to the traditional administration by injection of a small volume of vaccine (typically one to five mls) or antibiotic (limited to 10 mls per injection site for a large animal such as a cow or horse) have been developed. Most entail providing a sustained release formulation, such as EXCEED, which is injected subcutaneously once for release over a period of three to four days, or a stomach bolus, which dissolves over a period of two to three months after ingestion and passage into the rumen. Many of these are expensive, require prescriptions, and must be refrigerated or kept in the dark until used. Most also leave a drug residue, which can prevent sale of the meat or milk of the animal within a specified period.

Improper timing or amount can lead to a loss of efficacy and/or development of resistance in the case of antibiotics. This represents a loss not just of the direct costs associated with the capture and treatment and cost of agents to be administered, but may result in the animal failing to thrive or to die. Livestock that has been properly pre-conditioned by timely vaccination and parasite control brings a larger return since the costs associated with sick animals or animals that do not thrive are well established in the livestock industry.

It is therefore an object of the present invention to provide devices for single or multiple administration of therapeutic, prophylactic and/or diagnostic or identifying agents.

It is a further object of the present invention to provide devices which are single use, do not require refrigeration, and avoid the need for repeat administration.

SUMMARY OF THE INVENTION

A platform technology provides controlled delivery of single or multiple doses of therapeutic, prophylactic and/or diagnostic or identifying agents to livestock. The system avoids the need for traditional needle injections, by utilizing a modified livestock ear tag that releases therapeutic and/or prophylactic agent when pinned through the ear of the animal. The agent to be delivered is encapsulated/dispersed in microneedles and/or macroneedles (jointly referred to herein as "microneedles" unless otherwise specified) on a surface thereon of the male and/or female part of the tag, which is pressed into the skin so that the microneedles penetrate into the epidermis and dermis. The agent is then released into the animal from the microneedles at the site of contact into the tissue.

The agents to be delivered are loaded or coated so that they are stable in the absence of refrigeration. The release kinetics can be tuned depending on the agents to be released. Typically, the agent, as a powder, liquid, particles (nano or microparticles) with or without matrix or excipient) is mixed with the material forming the microneedles, or the agent is used to form the microneedles, which are formed using techniques such as micromolding. The microneedles may be coated with a polymer or pH sensitive coating that helps to control and regulate release of the agent. The microneedles can be formed onto the surface of the male or female part of the ear tag, or as a separate one or multiple component piece that can be utilized with commercially available ear tags. In another embodiment, the ear tag is a button or reservoir that is adhered to the ear by one or multiple posts. In another embodiment, the tag includes a reservoir for fluid delivery of agent. In yet another embodiment, an elastomeric membrane, hydrogel and/or adhesive structure to allow transfer of agent into the skin is used instead of or in combination with the microneedles. In yet another embodiment, the tag has a spring within the male member that pushes the microneedles into the ear. There may be more than one microneedle base, to provide for multiple administration of agent. In another embodiment, the microneedles may be partitioned into different regions, which are formulated to accommodate different rates of release of one or more agents. The microneedles may be mixed in content (one or more different agents for delivery) and/or size or composition to provide for different rates or amounts of release of agent, for example, using macroneedles for release of one agent or immediate release, in combination with microneedles for delayed pulse release, or vice versa. In another embodiment, the delivery system resembles the metal clamp brucellosis USDA tags, where instead of piercing the ear with two interconnecting components, they are clamped with a "U" shaped tag and piercing elements on the open ends of the "U" onto an edge of the ear.

Examples of agents to be administered include vaccines against diseases such as bovine respiratory disease (BRD), which is particularly a problem with stressed or young animals, antibiotics or trace nutrients. Administration into the epidermis and dermis layers of the skin promotes maximum immune response due to a naturally higher concentration of Langerhans antigen presenting cells, a critical class of cells that are part of the innate immune system.

The tags can be applied using commercially available applications, such as those sold by ALLFLEX. The male member is positioned on the shaft of the alignment pin while the female member is clamped onto the opposing member of the applicator. The tag is positioned on the ear, with the microneedle surface adjacent the male member preferably placed on the inside or front of the ear, and the applicator is engaged by applying compressive force to the handle grip until the male member shaft penetrates the receiver of the female member and is retained by the shoulder therein.

BRIEF DESCRIPTION OF THE DRAWINGS

FIG. 5A is an expanded view of the components; FIG. 5B shows the clamped assembled ear tag.

FIG. 6C shows a cross-section of the sleeve and depicts multiple layers each with different purposes that contribute to independent release rates of an agent as previously described.

FIGS. 9A and 9B are cross-sectional views of a button type of device, containing a spring that presses an array of microneedles into the device after the device shaft penetrates the ear. FIG. 9A shows the recessed microneedle base; P FIG. 9B shows the deployed microneedles.

FIG. 15B in a perspective view), to provide delivery of agent to different regions of the ear. This configuration may also be used to pre-perforate the tissue thus preparing an enhanced agent diffusion pathway.

FIG. 16 is a schematic of the ear tag where there are multiple posts, each which can be loaded or coated with a combination polymer and or agent and each with a unique programmed release rate or timepoint, such as t=0 and t=45 days.

FIGS. 17A and 17B are schematics of an ear tag where the microneedle arrays are designed to engage the tissue target as isolated and elevated geometries that prevent the entire horizontal base from engaging with the tissue. The base may have perforated or otherwise porous patterned sections so that the ear tissue that is not engaged with the microneedles is in direct contact with light and air as shown in FIG. 17A. FIG. 17B has raised microneedles but the base is not an open architecture as is FIG. 17A. It does, however, have adequate ventilation channels to allow free movement of air around the microneedles and adjacent tissue. This embodiment is particularly useful to avoid pressure necrosis, especially on large surface area microneedle arrays. FIG. 17C is a cross-sectional view of the base in FIG. 17B.

FIG. 19B side view).

DETAILED DESCRIPTION OF THE INVENTION

I. Delivery Systems

Figure 1:
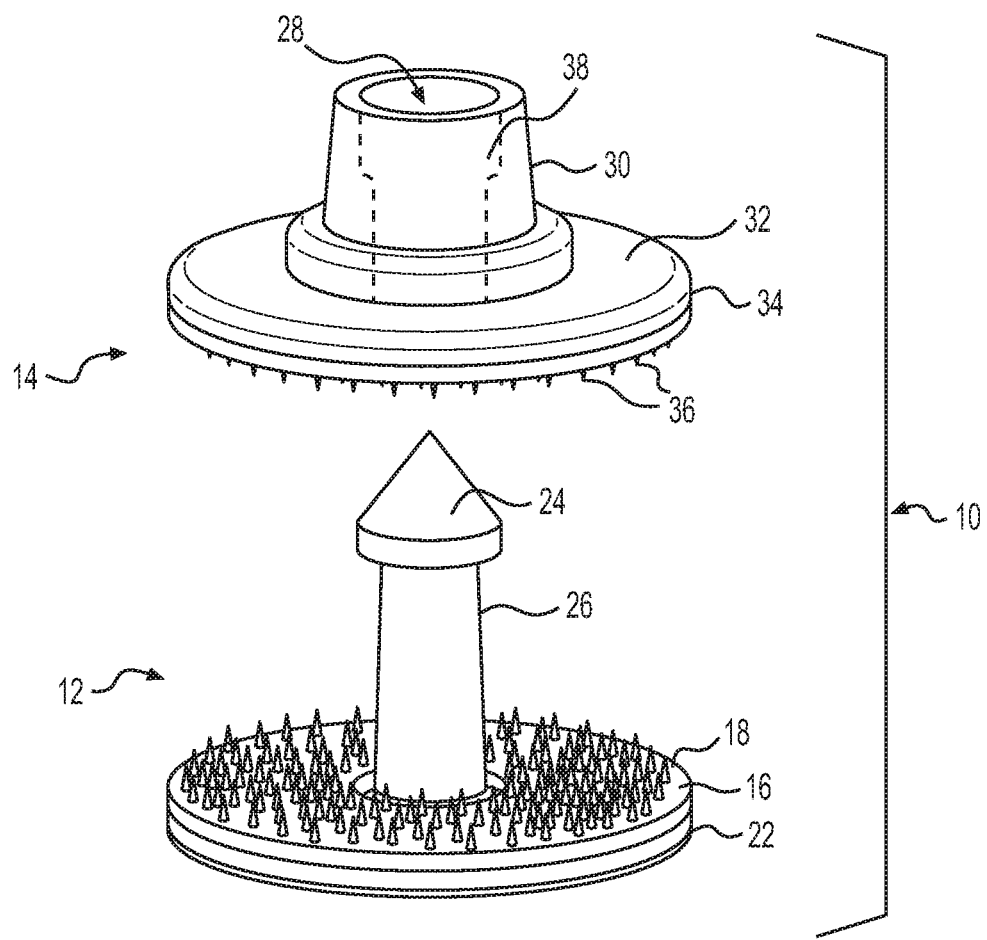
FIG. 1 is a schematic of an ear delivery tag, including a male and female member. The male and/or female members incorporate agent to be delivered and has a flat planar surface with uniformly located microneedles therein, for release into the skin when pinned together. The microneedle array is always a separate part. It may be pre-loaded onto the tag by the manufacturer or it may be provided as a separate component that is attached to the male or female tag component by the applicator just prior to device deployment.

There is a clear need for a single administration, multi-dose delivery device for therapeutics such as antibiotics, prophylactics such as vaccines, trace minerals and micro-nutrients, and diagnostic and/or agents for identification, especially for use with food livestock including bovine, ovine and porcine species, although the technology could be used for other animals, including domestic pets and feral animals. In most instances the devices do not require cold storage and are intended to maintain viability and effectiveness in a wide range of thermal and moisture exposure conditions. Each device is used on only one animal, thereby eliminating risk of "next-in-line" pathogen transfer via multiple-use needles as is common in the current state of the art.

The devices are particularly useful for certifiable pre-conditioning verification to assure buyers etc. that calves have been fully vaccinated, and have the benefit of zero ingredient residuals in or tissue damage to food parts, all of which are value adding.

In summary, this platform ear tag delivery technology has a wide range of applications, material choices and application locations, for delivery of vaccines, drugs such as antibiotics, trace minerals, probiotics, etc. with highly tunable release kinetics, which is minimally invasive, easy to administer, with no special training required, having multiple possible forms and mechanisms either singly or in combination to be employed, and include embodiments where the act of piercing the ear and/or the selection of the materials forming the microneedles and/or ear tags acts an a adjuvant. An advantage of the device is that it provides targeted delivery to the epidermis and dermis layers of the skin as opposed to sub-cutaneous or intramuscular delivery, which is ideal for achieving maximum immune response. Another advantage is that the device is capable of delivering multiple materials each with independent release kinetics. These tuneable release kinetics may be continuous, pulsed, and/or delayed.

A. Ear Tags

The ear tags utilize existing technology for identification of livestock, to minimize reeducation of users and to take advantage of available means of application. However, it is understood that alternative methods for administration may be used with some embodiments, especially those in which larger amounts of agent is to be delivered.

Livestock ear tags are commonly used for animal identification. There are many manufacturers that sell identification tags, insecticide tags, hormone ear implants and tissue biopsy devices. Tags are commonly applied to young animals and ideally remain in place for life. Often, more than one tag is used. Tags containing for example, 40% diazinon organophosphate, are used for fly control. Electronic identification (EID) tags are growing in popularity and tags are also being developed to support physiologic monitoring technology. Such a ubiquitous use of tags and the fact that they are applied to the ear, one of the least hair-covered parts of livestock bodies, makes them a useful foundation to deliver therapeutics.

Example 1: First Embodiment of Ear Tag for Delivery

As shown in FIG. 1, the system 10 has a male member 12 and a female member 14. The male member 12 includes a planar surface 16 having uniformly distributed thereon microneedles 18 extending outwardly at a perpendicular angle and a support base 20 which may also serve as a reservoir 22. A pointed tip 24 is connected via a shaft 26 to the planar surface 16 and support base 20. The female member 14 has a receiver 28 in a shaft 30 connected to a support base 32 having on its outside surface 34 a uniform distribution of microneedles 36. The microneedles extend perpendicularly from the base and in parallel to the male portion shaft.

The shaft 26 is inserted through the ear into the female member 14 so that the tip 24 penetrates the receiver 28. The receiver 28 includes a shoulder 38 that snaps under the tip 24 to secure it within the receiver 28. The shaft can be round, square, rectangular, triangular or other shape. The length is designed for the animal to which the tag is to be applied, with the understanding that adult cattle ears are thicker than calf ears, and that pig and sheep ears are similarly unique. The length should be sufficient to penetrate through the ear and fully into the receiver, but not so long that the microneedles are unable to securely contact the skin of the ear and penetrate into the tissue. This variable can be controlled with an animal/species dependent spacer which ensures appropriate microneedle engagement.

The male member in this embodiment contains the therapeutic or prophylactic agent to be delivered. loaded into and/or onto the planar surface, the support base and/or the microneedles. The female member 14 may also have microneedles for delivery The male member 12 has agent to be delivered loaded into and/or coated within the microneedle array 18, a generally flat base 16, 22 minor axis and round, square, rectangular, triangular or other shape major axis with a central hole 28 in the female member 14 that, when aligned with and attached to the male member 12, slides over the male member shaft 24, 26 and seats on the male member base 16 where it is attached. The microneedle array 18 protrudes from the base surface 16 so that the needles 18 extend perpendicularly from the base 16 and in parallel to the male portion shaft 26.

In this embodiment, the male member 12 engages through the front of the ear so that the microneedles 18 are not encumbered or obscured by hair. The female member, 14 which may or may not have a microneedle array 36 affixed to it, has a base 32, 34 and a hollow receiver 30 that has an internal shoulder 38 that when received by the male member 12 allows the tip or head 24 of the male member 12 to irreversibly snap into position, thereby locking the two members 12, 14 together and forcing the microneedle array 18, 36 into the ear tissue.

Example 2: Second Embodiment of Ear Tag for Delivery

Figure 3A:
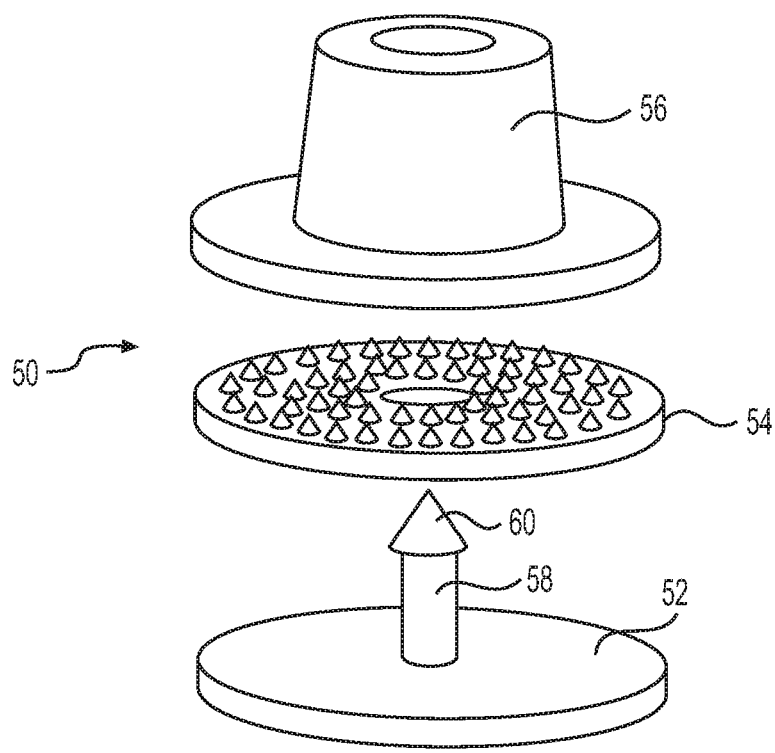
FIGS. 3A and 3B are schematics of a second embodiment of the ear tag, showing assembly (FIG. 3A) and assembled tag (FIG. 3B) where a therapeutic member is inserted into a conventional ear tag.
Figure 3B:
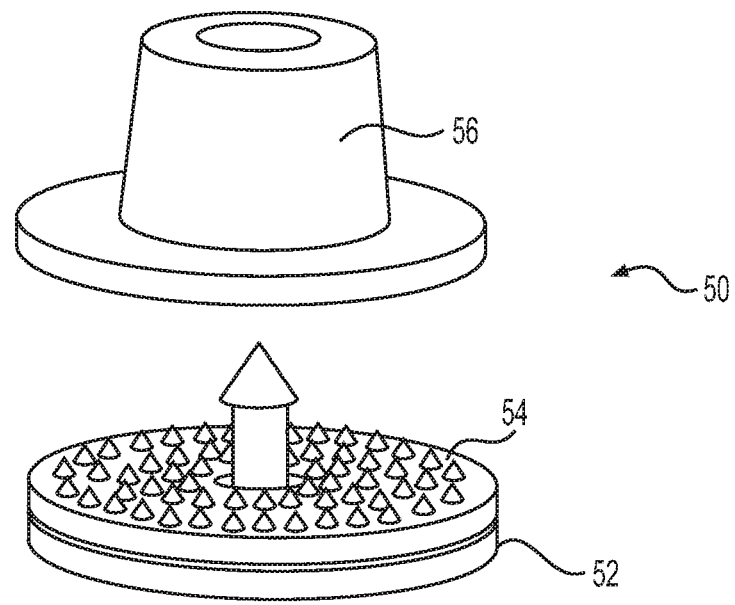

FIGS. 3A and 3B depict a second embodiment 50 in which the therapeutic member 54 is separate from the male support member 56 with shaft 58 and tip 60 and female member 56. This allows for use of the therapeutic member 54 with currently available ear tags to form a composite device as shown in FIG. 3B.

Figure 2:
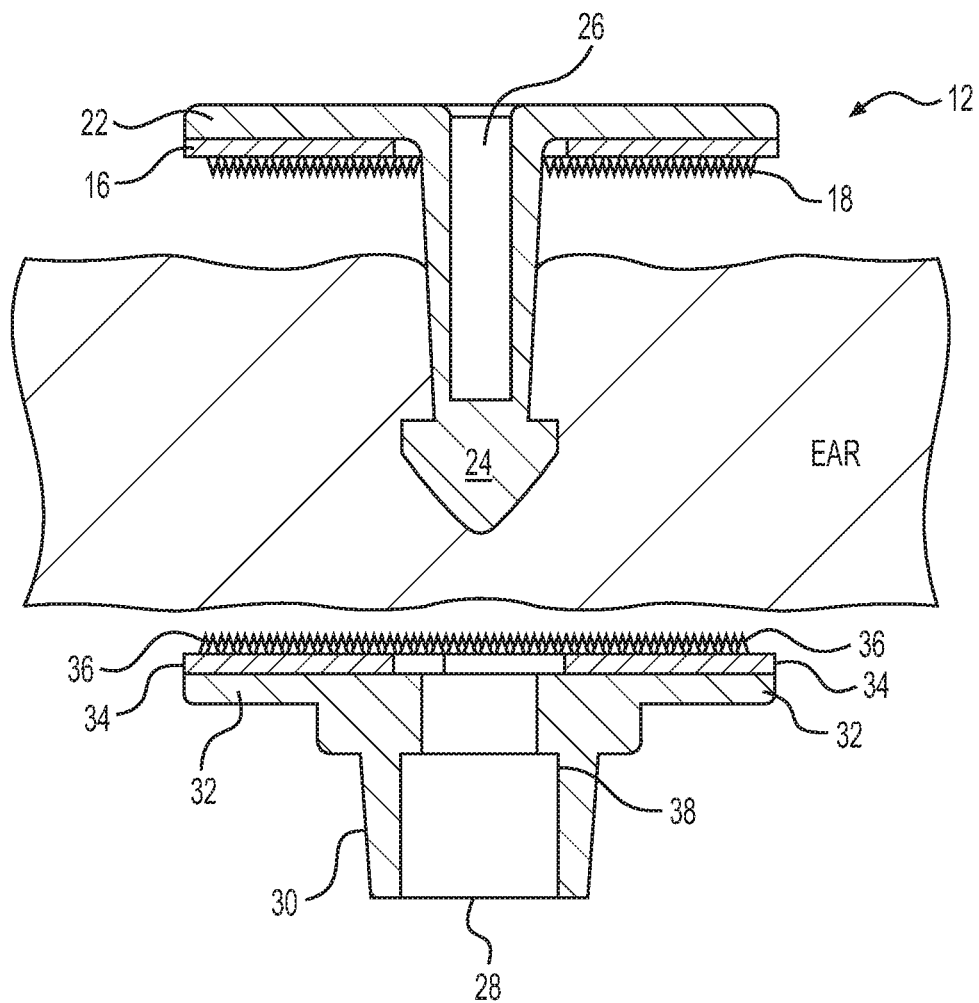
FIG. 2 is a schematic of the insertion of the shaft and tip of the male member into the female member of the ear tag of FIG. 1.

Like the affixed therapeutic member shown in FIGS. 1 and 2, the separate therapeutic member 54 slides over the male portion shaft 58 and rests on the base 52. This ensures that the separate therapeutic member 54 remains on the male portion shaft during application. An additional snap-fitting element that prevents disengagement may also be used.

Example 3: Third Embodiment of Ear Tag for Delivery

Figure 4A:
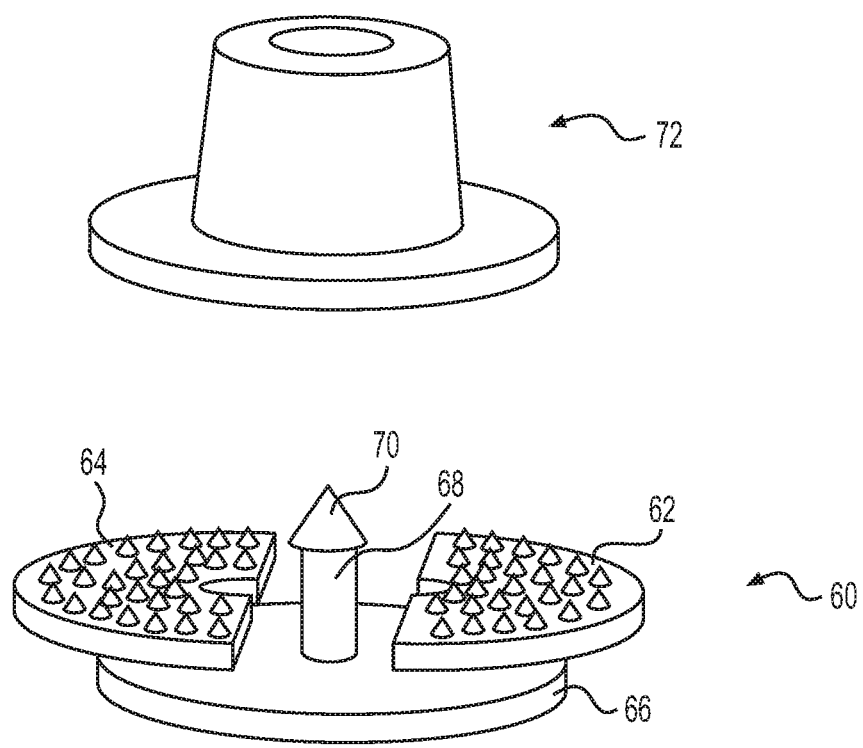
FIG. 4A is a schematic of a two region insert for use with a conventional ear tag.
Figure 4B:
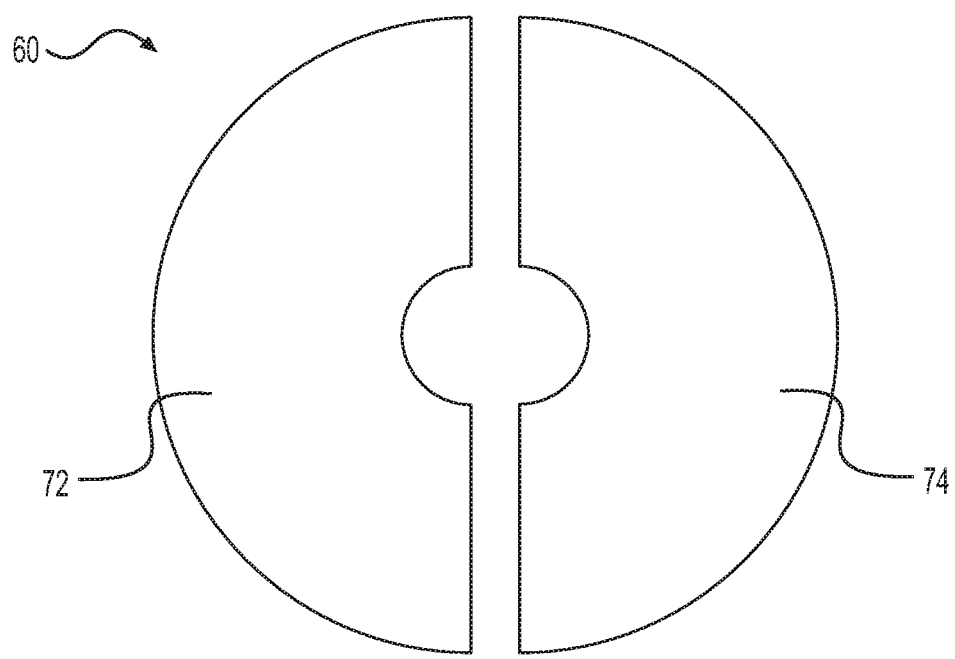
FIG. 4B is a schematic of two individual hemispheric component microneedle arrays, one with one programmed time of release (t=0 in gradient x) and a second with a second programmed time of release (t=x in gradient y).
Figure 4C:
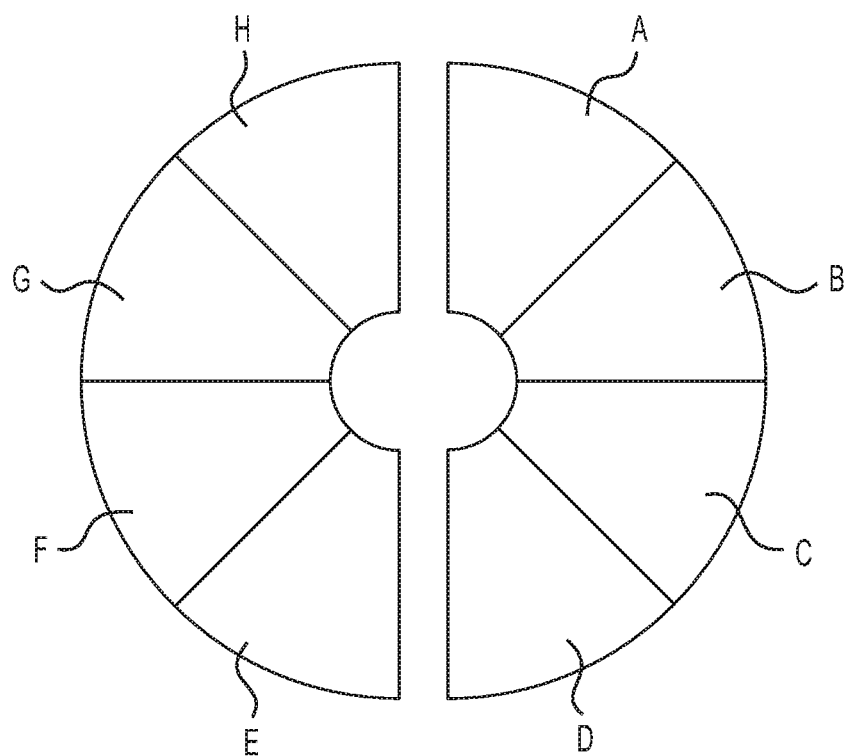
FIG. 4C shows multiple individual inserts, each which may be programmed for release of different agents, such as different antigens all of which may have matching or independent release rates.

In this embodiment 60, depicted in FIG. 4A, two separate therapeutic members 62 and 64 are utilized as an insert for use with a conventional ear tag. FIG. 4B is a schematic of the piece where there is a region with one time of release and a second with a second time of release. FIG. 4C is the insert with regions for release of different agents, such as different antigens and, if desirable, different PK/release profiles. These regions may have different release kinetics due to loading of agent, due to thickness of the region (thicker will provide longer term release), through the use of materials such as a biodegradable polyester with a period of weeks to months for degradation compared to, for example, a sugar matrix that releases within a few days at most, the use of an enteric coating and a pH modifier, or a water soluble coating which dissolves in contact with blood or interstitial fluid released when the ear is punctured.

These members 62, 64 are attached to the base of the male 66 or female 72 members to form ear tag 60. Each member can be loaded with the same, different or combined agent, dosages or release kinetics. Each member 62, 64 may have the same or different or multi release kinetics that allow for highly tuned therapeutic substance delivery at specific time points from t=0 (time of deployment). For example, referring to FIG. 4B, a primary dose of vaccine may be delivered at the time of deployment, t=0 in gradient x, of microneedle array 72, the delivery rate of the primary dose may be programmed for immediate release, or it may be programmed at any desired rate of delivery, which provides the desired initial IgM immunologic memory stimulus. A secondary or booster dose may be delivered at, for example, 45 days, referring to FIG. 4B 74 (t=x in gradient y), to provide an IgG immunogenic escalation to reach and maintain immunoprotection above a minimum therapeutic index. There may be any number of therapeutic members attached or attachable to the male and/or female members of the tag. For example, there may be one therapeutic member or there may be two, three, five, ten or more individual and independent therapeutic members, each highly tunable in terms of what substance they are loaded and/or coated with, what release kinetics each member exhibits, and what quantity of substance each member contains. The microneedle array elements 62, 64 may contain regions of different agents, different amounts of agent(s), have different kinetics, or a combination thereof, as shown in FIG. 4C.

Example 4: Device with Non-rigid Membrane for Transfer of Agent

Figure 5A:
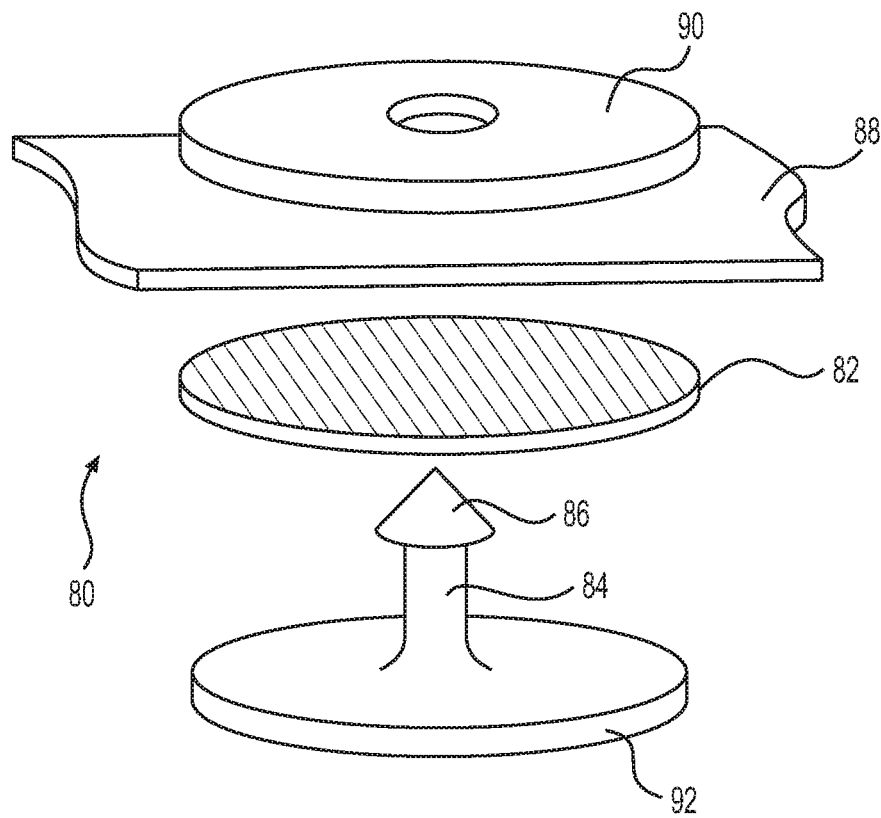
FIGS. 5A and 5B are schematics of an ear tag with an elastomeric or adhesive membrane which may take the place of microneedles, to contact and transfer agent(s) loaded into the therapeutic membrane which deforms during ear penetration and forced into contact with the animal's ear via the exposed tissue opening created by perforation.
Figure 5B:
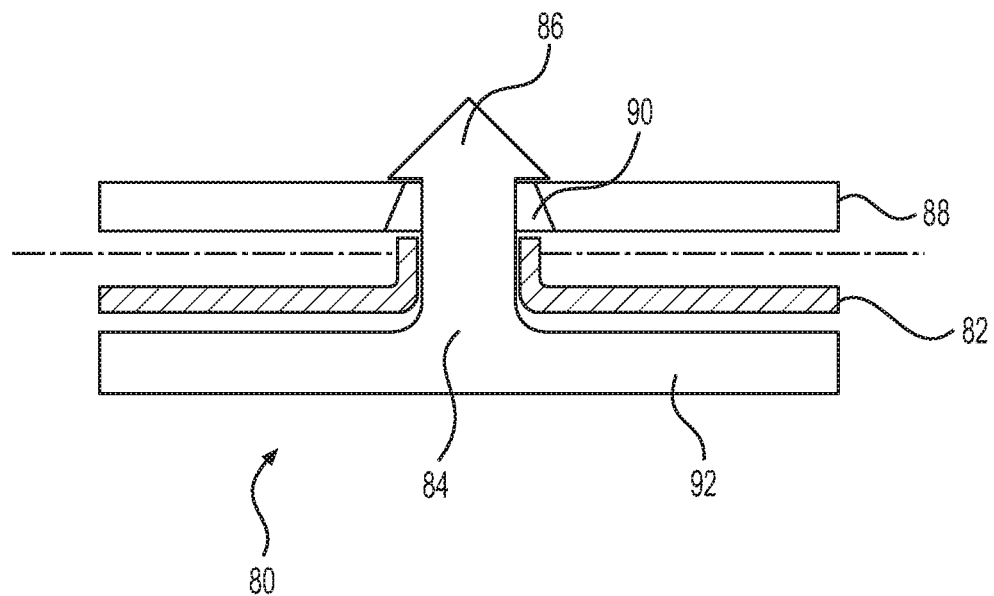

As shown in FIGS. 5A and 5B, this device 80 uses the tissue penetrating action of the tip 86 of central shaft 84 of existing rigid tags to position a stretchable hydrogel membrane, 82 into close contact with the wound site that results from standard tagging. The goal of this design is to have close contact between the delivery vehicle and the tissue for an extended period of time (months). Long-term contact is required to enable a secondary pulse of the vaccine. In this design a standard ear tag serves as a one-time applicator of a soft, conformable hydrogel membrane 82 that is initially attached to a rigid backing 88, then released from 88 upon application and then incorporated into the wound area generated by tag penetration of the tissue. The tag shaft 86, 84 can stretch and pierce this membrane in the same action as it pierces the tissue, thereby depositing it directly over the entire open wound area. The more rigid membrane backing layer 88 sticks to the tag 90 and leaves behind the fully conformable membrane. After this action the rigid components 92, 88, 90 remain engaged with the tag backing while the highly conformable backing remains directly adhered to the tissue. In this manner, all the rigid components stay associated with the standard ear tag, which is loosely engaged with the ear as is standard. This loose engagement of the rigid components prevents pressure necrosis. The conformable membrane 82 is designed to stretch and form to the tissue and may be resorbable and incorporate vaccine or vaccine particles (e.g. pulsatile cubes) that become embedded in the tissue during wound healing. Membrane 82 is therefore designed to be unable to cause tissue pressure necrosis, as it is not rigid.

Example 5: Ear Tag with Multi-Dose Center Shaft Reservoir

Figure 6A:
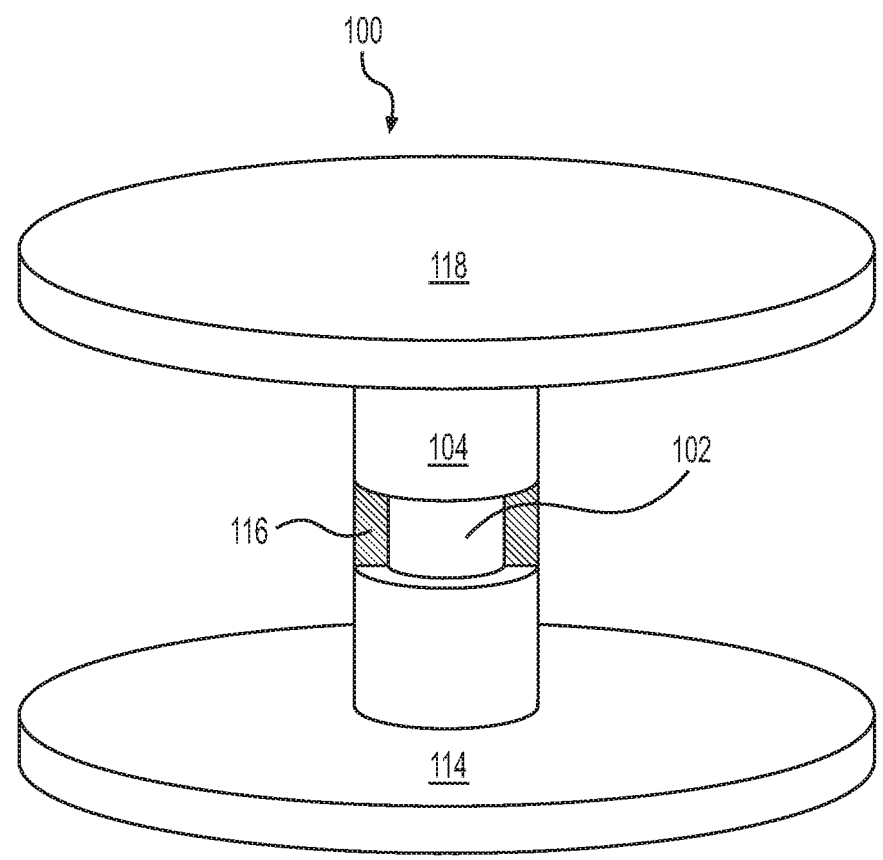
FIGS. 6A-6C are schematics of an ear tag with an agent loaded sleeve located on the center male shaft, showing how another tissue access approach is used to control perpendicular release into the tissue relative to the planar surface of the ear which is opened at the time of piercing the ear, obviating the approach of using microneedles to pierce the skin on the planar surface of the ear.
Figure 6C:
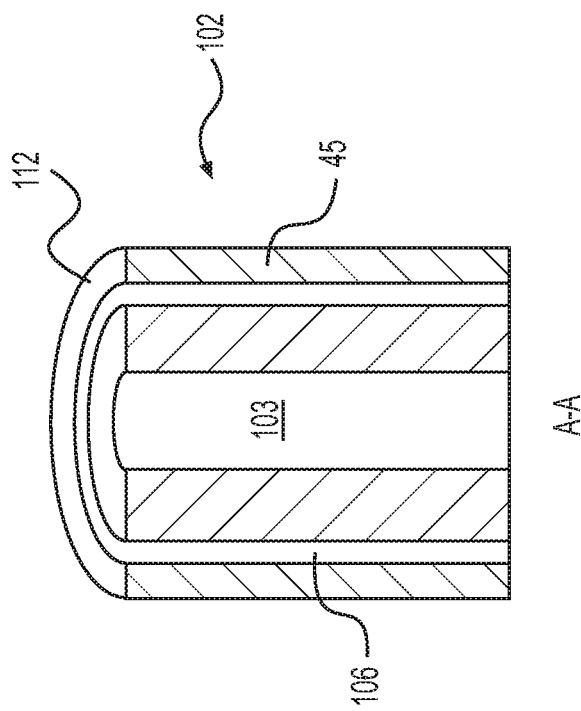
Figure 6B:
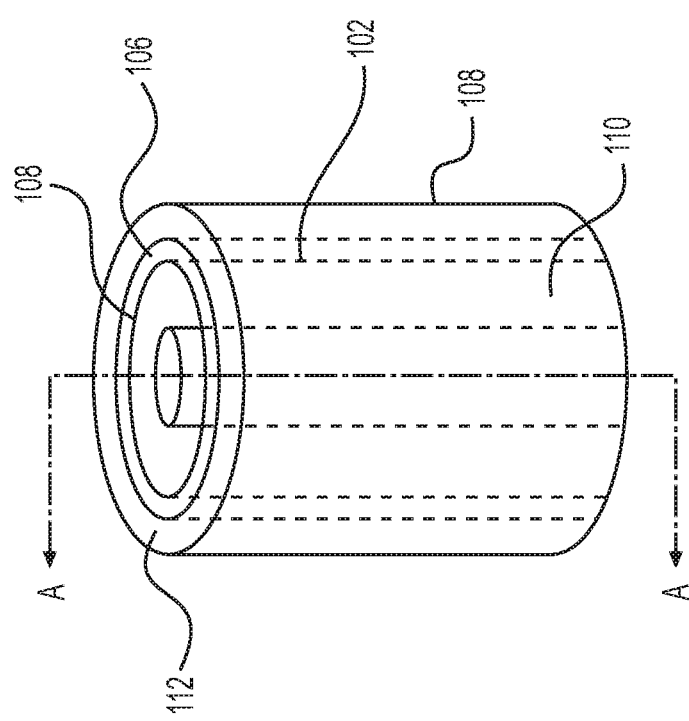

In another embodiment that also embraces a standard tag platform, the shaft of the male member provide a depot for the active agent, which, for example, may include antigen, adjuvant and/or excipient. FIGS. 6A-6C are schematics of an ear tag 100 with reservoir 102 in the center shaft 104, showing how a rate limiting membrane 106 (FIGS. 6B, 6C) is used to control release into the tissue which is opened at the time of piercing the ear, obviating the need for microneedles to pierce the skin.

This embodiment utilizes the tag itself as an adjuvant, based on the injury incurred during device delivery to the ear to provoke an inflammatory and wound healing response at the site, and allowing direct exposure of agent to the resulting injured, open tissue by which the primary dose is delivered at t=0. The section 112 housing the therapeutic substances can be made during injection molding of the male portion 114 of the assembly 100, resulting in a recess or circumferential slot 116 in the mid-section of the male member shaft 104 where it interconnects with the female member 118. In a separate operation, the active agent is loaded into or coated onto the depot using, for example, a tableting machine to create a cylindrical unit 102 with a hole 103 through the center that the male member 114 passes through as it engages with the female member 118. The agent loaded or coated cylindrical depot 102 rests on the shoulder of the male member 114 created in the injection molding process. The agent loaded cylindrical depot 102 has at least one or two or more delivery release components at, for example, t=0 and t=45+/− days. FIG. 6C shows a cross-section of the device of FIG. 6B, with the two dose 102, 108 layers separated by a degradation rate limiting membrane 106.

Example 6: Ear Tag with Expandable Central Shaft with Microneedles

Figure 7:
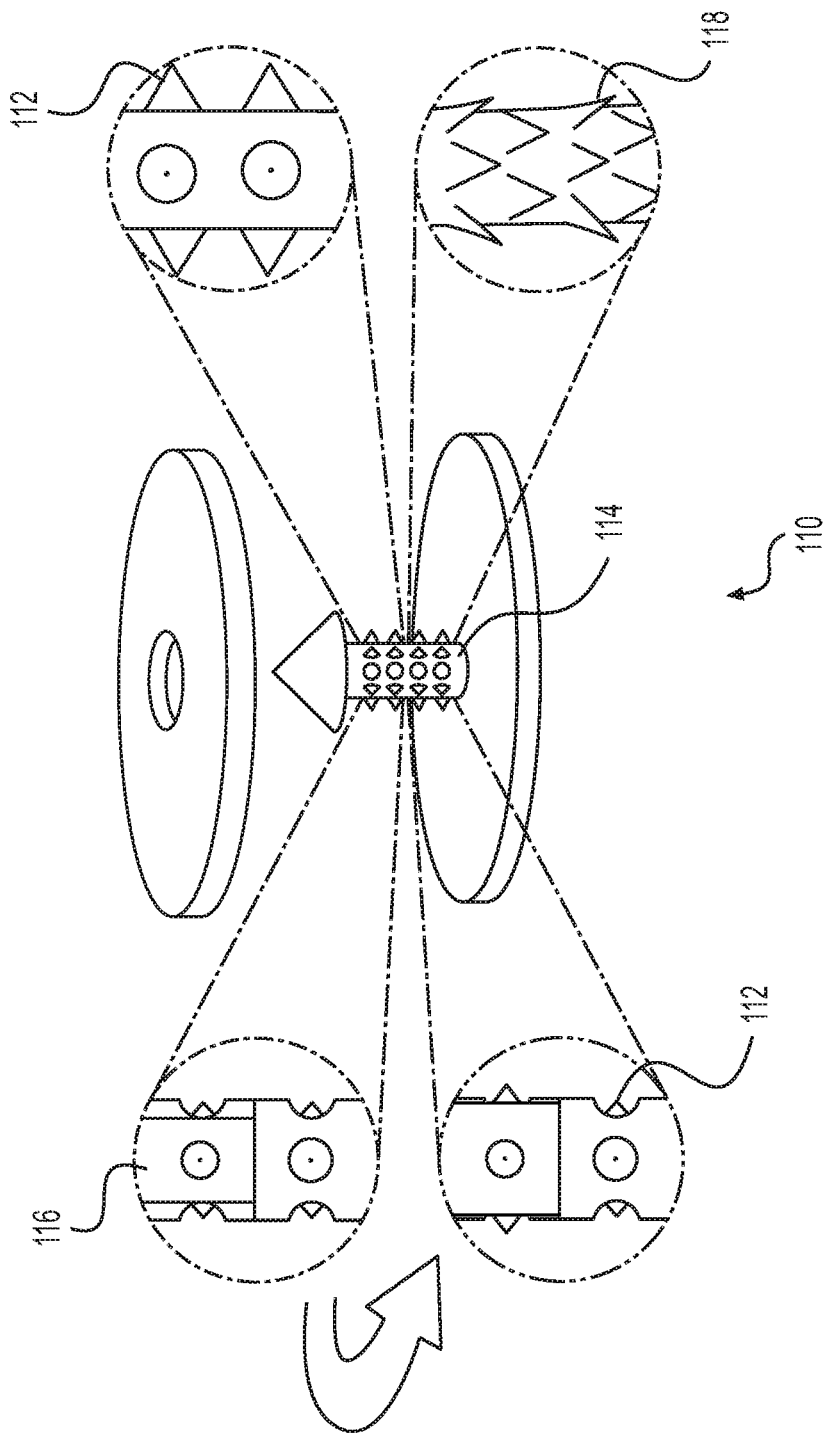
FIG. 7 is a schematic of an ear tag with microneedles on the shaft, which are expanded outwardly to penetrate into the dermis after the shaft penetrates the ear of the animal, for example, as shown in the expanded views, through the use of an expanding balloon or one-way barbed needles.

The device 110 in FIG. 7 has agent loaded or coated microneedles 112 protruding perpendicularly from the male member shaft 114. The microneedles 112 on the shaft 114 are expanded outwardly to penetrate into the dermis after the shaft penetrates the ear of the animal, for example, as shown in the expanded views, through the use of an expanding balloon 116 or uni-directional barbed needles 118. The shaft 114 acts as an adjuvant when it pierces the tissue of the ear, by exposing the wound tissue to the active released via the microneedles 112 on the shaft 114.

Example 7: Ear Tag with Detachable Micro or Macroneedles

Figure 8:
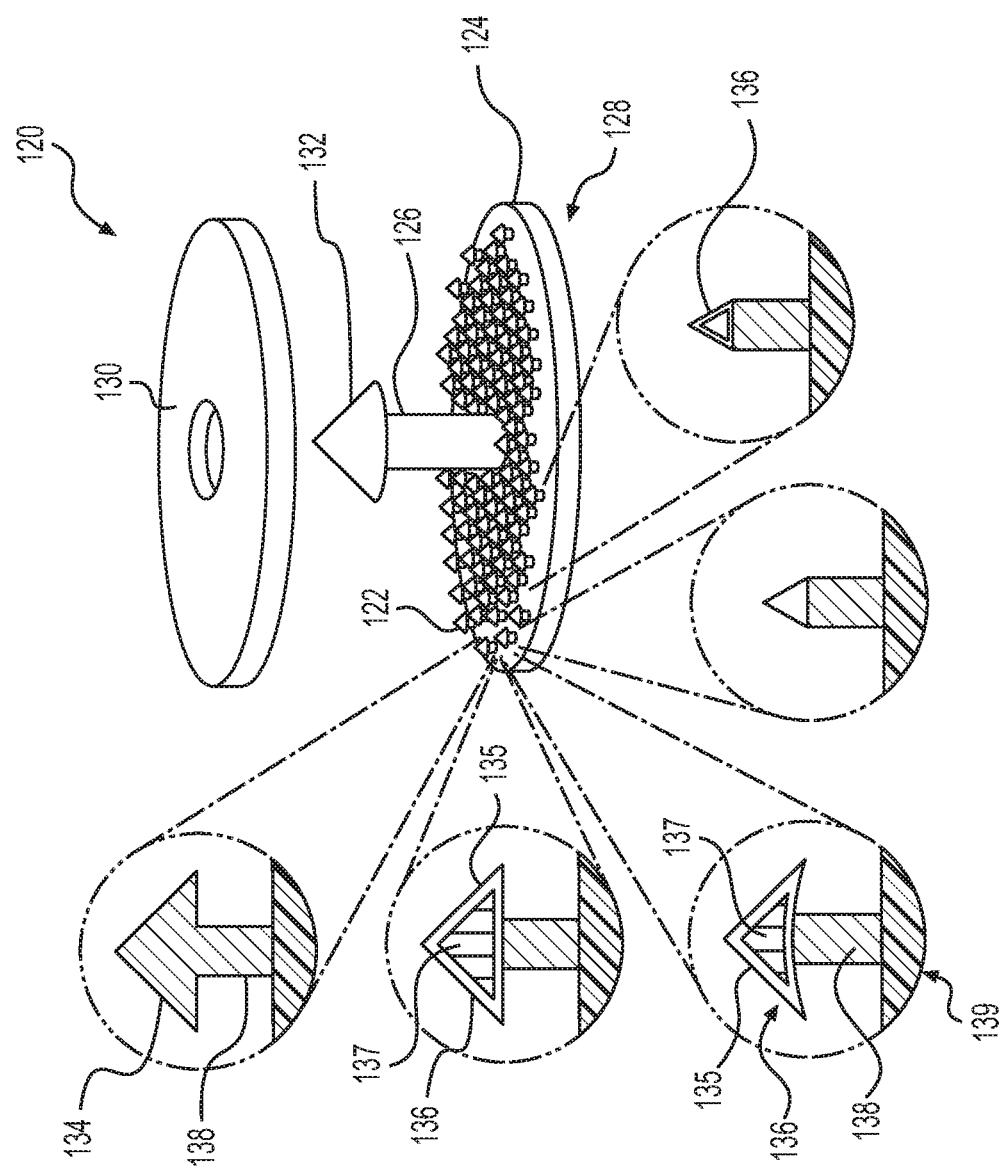
FIG. 8 is a schematic with expanded views of detachable microneedles that penetrate the epidermis and dermis (Global), then detach from the base of the ear tag, to remain embedded in the epidermis and dermis of the animal's ear where release is to occur.

This system functions as an ear tag while simultaneously implanting solid drug formulations into the epidermal and dermal tissues of the ear during application. FIG. 8 is a schematic of the ear tag 120 with expanded views of detachable microneedles 122 on the shaft 126 that penetrate the dermis, then detach from the base 124 of the ear tag, to remain embedded in the tissue of the animal's ear where programmed release is to occur.

The device 120 is comprised of two members, the male member 128 and the female 130. The male member 128 includes shaft 126 and tip 132. Shaft 126 penetrates through the entire thickness of the ear and engages with the female member 130 to affix the device to the ear. The male member 128 has protruding micro and/or macro needle structures 122 on base 124 that penetrate into the skin of the animal as the members 128, 130 are affixed to the ear. The macroneedles have, for example, a maximum 2 mm diameter and 1 cm in length. Microneedles have, for example, a diameter less than 400 μm and a length of 1 mm or less. Both can contain the agent to be delivered. Various needle designs can be incorporated onto the same device to achieve different drug delivery profiles and penetration strategies.

The first needle variants are formulated for immediate release of drug upon insertion into the ear. The needle structures are solid and designed to withstand the mechanical forces required to penetrate into the tissue. Following insertion into the tissue, the needles may dissolve rapidly to release a bolus of agent. In this embodiment, dissolution of the needle further allows healing of the skin at the implantation site to reduce risk of infection. Examples of this variant include a monolithic needle with agent suspended within a rapid-dissolving matrix (e.g., polyvinyl pyrrolidone (PVP), sugar, polyethylene glycol (PEG), uncrosslinked starches).

The second needle variants shown in FIG. 8 are formulated to release drug after a controlled delay following insertion into the ear. These are composed of a rapidly-dissolving stem 138 that supports a slow-dissolving drug-loaded needle head 134. The stem 138 rapidly dissolves following insertion into the ear, leaving behind the agent-loaded needle which remains lodged within the epidermal and dermal tissues. Dissolution of the stem 138 allows healing of the skin at the implantation site to reduce risk of infection. In one embodiment, the drug-loaded needle head 134 is composed of an agent-loaded core that is coated with an impermeable slow-eroding polymer film 136. This coating 136 delays release of drug contained within the core 137 for a fixed amount of time following needle insertion into the ear.

An example of this needle variant 139 includes a rapid dissolving stem 138 (e.g., sugar, PEG, PVP, uncrosslinked starches), and a needle head 136 composed of drug suspended within a rapidly-dissolving matrix that is further coated with a hydrophobic slow-eroding polymer film 135 (e.g., polycaprolactone (PCL), polylactic acid glycolic acid (PLGA)). The structure and thickness of the hydrophobic film can be tuned to achieve the desired drug release delay following insertion into the ear.

In a preferred embodiment, the needle structures are large macroscopic needles to maximize drug loading capacity, increase mechanical durability of the device, and ensure placement of the drug-loaded portion of the needle at the correct tissue depth.

Example 8: Spring Loaded Microneedle Button

FIGS. 9A and 9B are cross-sectional views of a button type of device 140, containing a spring 142 that presses one or more layers of microneedles 144 into the device agent after the device shaft penetrates the ear. FIG. 9A shows the recessed microneedle base 144; FIG. 9B shows the deployed microneedles 146.

The film 148 seals the inside of the device 140 from the ambient environment and ensures that the internal environment is moisture free. Inside of the device is a microneedle array 144, a compressed spring 142, and an actuation mechanism (not shown). The microneedle array 144 is made from a hydroscopic biocompatible material such as PVP or Sorbitol, and possesses microneedles 146 between 500 µm to 1200 µm in height. The microneedles 144 and 146 can be spaced within 300 µm of each other. The compressed spring 142 delivers between one and 20 N of force.

To ensure that the microneedle patch engages with the tissue, the patch must contact the tissue. If the device is left loose on the animal's ear, then the microneedle patch will need to extend out of the device to contact the tissue. To ensure that the microneedle patch passes out of the device while moving in a one dimensional path, the patch must be connected to a long base plate 150 that is approximately the same diameter of the device and be at least 0.1× the length of the device. The base plate should be made of a rigid material, for example polystyrene or polycarbonate, so that it does not morph when pressure is applied.

The actuation mechanism can be actuated manually or automatically to release the compressed spring. A tab may be used to hold the microneedle patch, connected to a sturdier base plate, in place and keep the spring in compression. The tab, when manually removed, allows the spring to expand and the device to actuate. Alternatively, the tab can be removed or dissolved after actuation of the device via an electrical signal. Electronics in the device could communicate with other devices such as a controller or a cell phone via Bluetooth or near field communication. Another method of actuation is to encapsulate the compressed spring in a hard material. The spring actuates once the encapsulation material is dissolved or melted. Melting could occur by generating heat by passing current through an electrical wire. Dissolution of the material could occur by bringing the material in contact with a previously encapsulated liquid such as water. This liquid could be manually applied or a barrier could be removed via remote actuation to reveal the liquid, or the fluid could be blood or interstitial fluid at the site of administration through the ear.

Figure 10A:
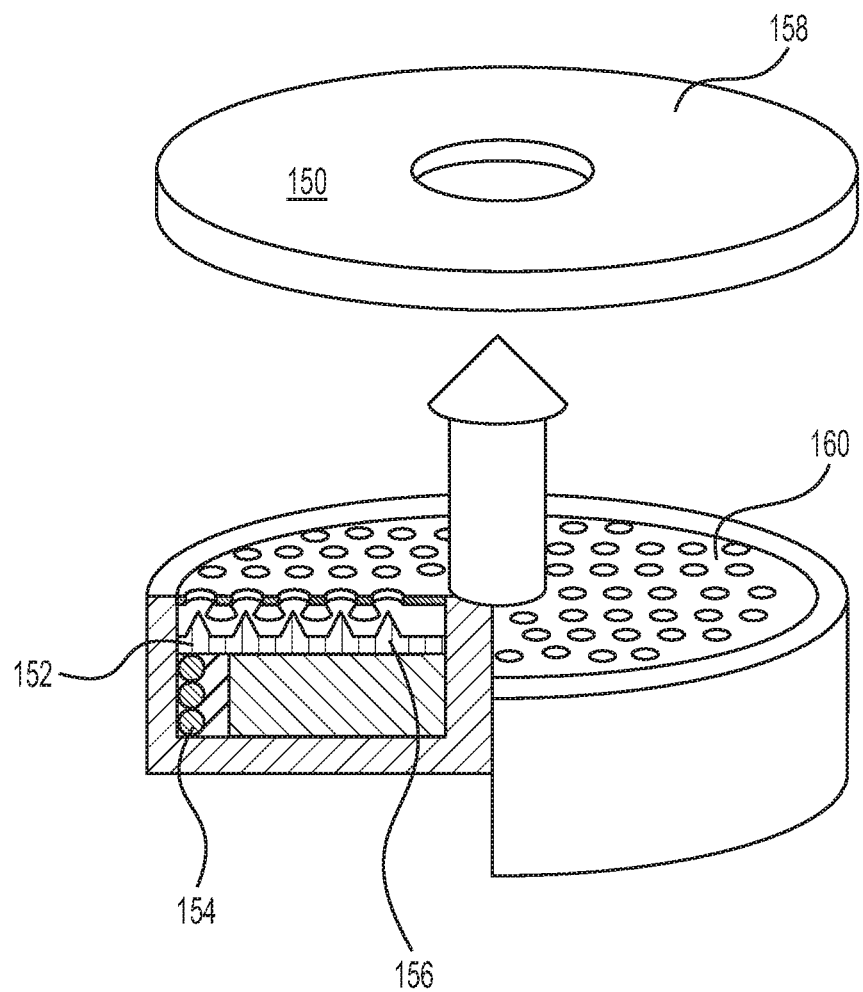
FIGS. 10A and 10B are prospective views of the spring loaded devices of FIGS. 9A and 9B, including a triggering mechanism and unloaded spring. The ejection mechanism serves to protect the microneedles during storage in an enclosed compartment up until administration.
Figure 10B:
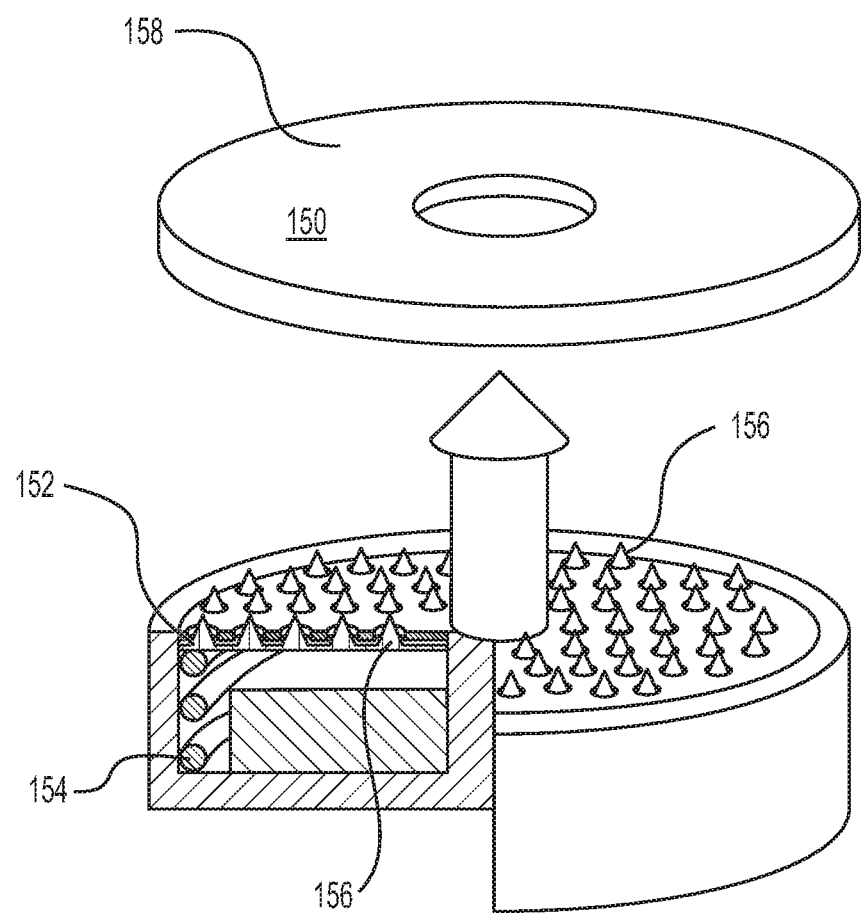

FIGS. 10A and 10B are prospective views of the spring loaded devices 140 of FIGS. 9A and 9B, including a triggering mechanism and unloaded spring as discussed above. These devices include one or more disk-based mechanical secondary injection mechanisms for repeated injection of a therapeutic.

Microneedles are mounted on one or more moving bases 152 that are each attached to a spring 154 that can move the base 152 and inject the microneedles 156 into tissue. The spring 154 is retained in its compacted form by a trigger mechanism not shown. Preferably the trigger mechanism is a material that dissolves or erodes in the presence of water, such as a sugar coating that immerses the spring in solid state. Upon inflow of water the sugar dissolves and releases the spring thereby triggering injection. In one embodiment the water inflow into the device is controlled by a coating. The coating preferably contains a degradable polymer preferably polycaprolactone or poly(lactic-co-glycolic acid) (PLGA). Most preferably the coating contains a water permeable but not soluble coating such as ethyl cellulose or cellulose-acetate. The triggered mechanism more preferably is an electric circuit. Preferably the electric circuit is activated by the presence (or absence) of a magnet 158 in plate 150. The magnet signal is preferably transduced with a reed switch. Upon activation the electric circuit mechanically releases the spring 154 and the system injects the microneedles. The part through which microneedles are injected into the tissue preferably comprises a water retaining membrane 160 to protect microneedles from degradation. The membrane preferably contains aluminum.

Example 9: Clip on Ear Tags

Figure 11:
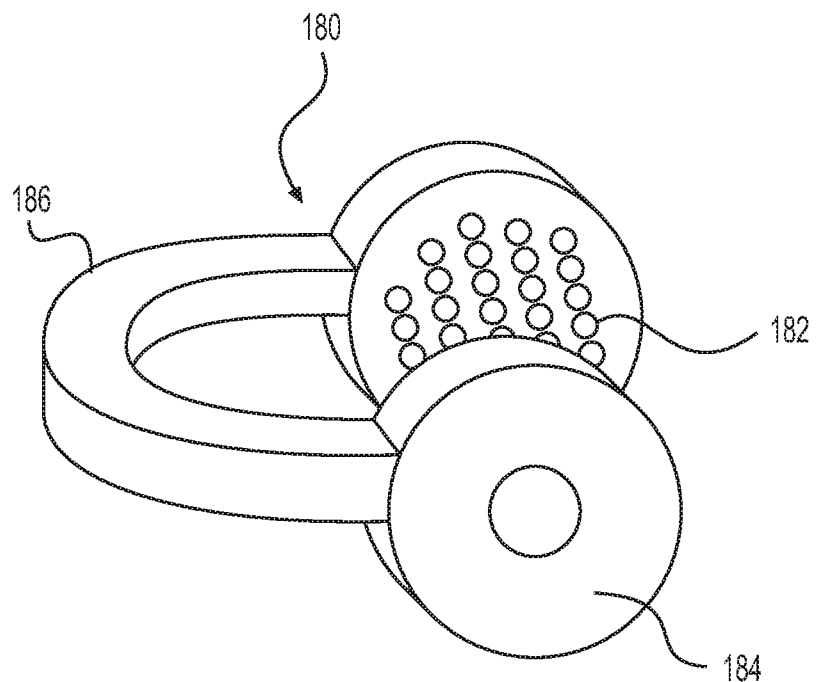
FIG. 11 is a schematic of a clip on ear tag, where the two support bases are secured on either side of the ear to release agent from the microneedles.
Figure 12:
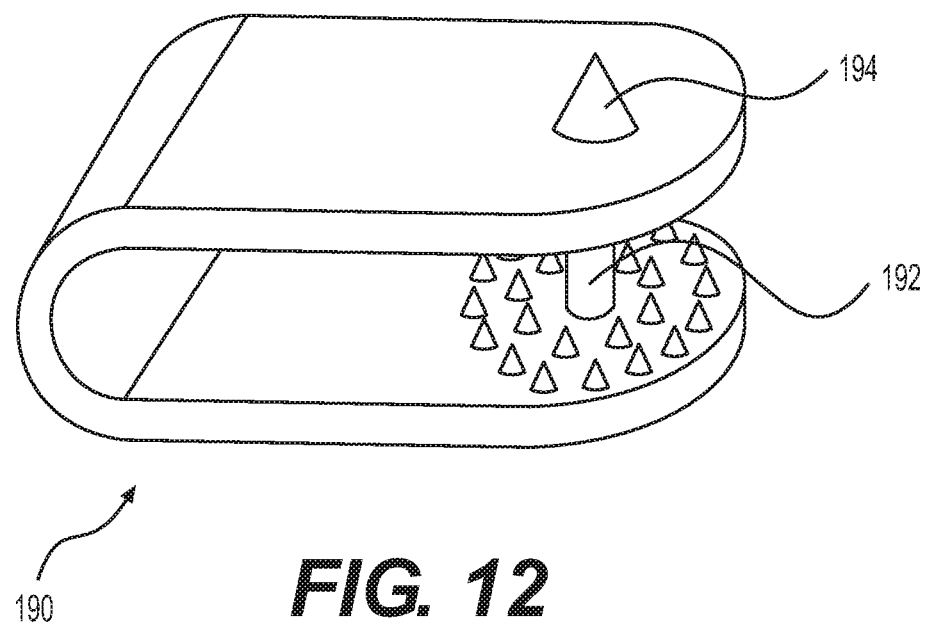
FIG. 12 is a schematic of a variant of the device of FIG. 11, comprising a shaft that penetrates the ear to secure the microneedles into the dermis for delivery.

FIGS. 11 and 12 demonstrate clip on ear tags, rather than penetrating ear tags, where the two support bases are secured on either side of the ear to release agent from the microneedles. FIG. 11 shows a clip on ear tag 180 which is U-shaped with two opposing therapeutic loaded or coated microneedle bearing surfaces 182, 184, that, when the plastically deformable or shape memory U-member 186, made of a material such as 316-L stainless steel or shape memory NiTi alloy, is manually manipulated, causing engagement into the ear tissue where the microneedles 182 penetrate the tissue and release active in a singular or multi-staged profile.

Multiple clips maybe administered. They may be color coded to identify different properties, release profiles, agents, etc.

Another version of the clip 190 is shown in FIG. 12, which includes a shaft 192 and tip which penetrates the ear, wounding the tissue and enhancing the immunogenic response while simultaneously delivering pulsed agent at one or more timepoints. The shaft 192 and tip 194 also help to secure the chip on device 190.

Example 10: Reservoir Ear Tag

Figure 13:
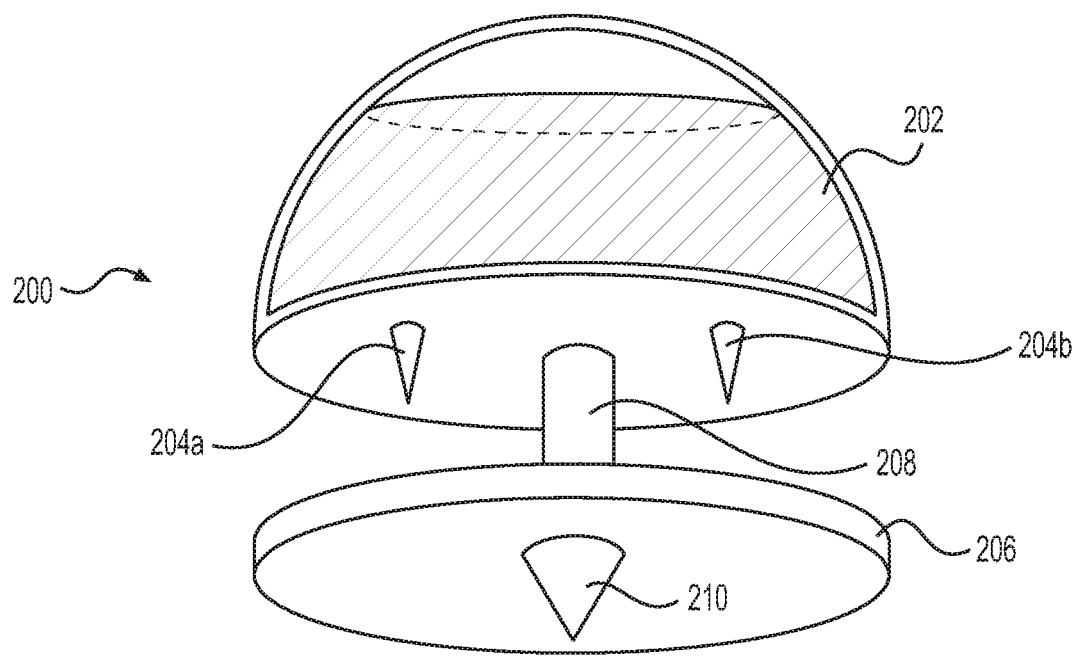
FIG. 13 is a view of a button reservoir that has two macroneedles that, being hollow to allow liquid transport, are functionally equivalent to syringe needles, which penetrate into the ear when the shaft penetrates into the ear and is secured, allowing the fluid in the reservoir to enter the ear.

FIG. 13 depicts a reservoir device 200 that houses an environmentally isolated hollow body 202 that may be loaded and filled with an agent to be delivered. Shaft 208 with tip 210 penetrates the ear and is secured by female member 206. Two macroneedles function as ports 204a, 204b which are functionally equivalent to syringe needles, and penetrate into the ear when the shaft 208 and tip 210 penetrate into the ear and are secured, allowing the fluid in the reservoir to enter the ear.

Figure 14:
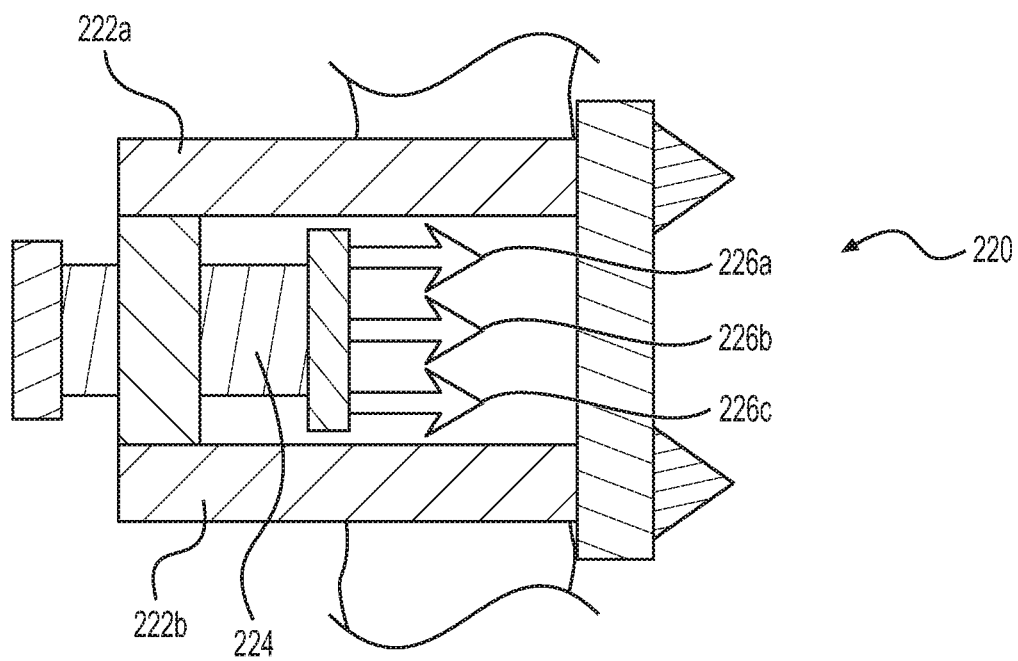
FIG. 14 is a cross-sectional view of a delivery device that has two or more shafts that penetrate the ear to secure the device. A series of agent are loaded or coated onto or into microneedles and the microneedles are attached to a central plunger that passes through a back plate. A shoulder on the back of the plunger retains a spring which is held in a compressed position by a resorbable polymeric coating during administration and for a programmed time period at which time, when the polymeric coating fractures and frees the spring, allows the plunger to rapidly advance and engage the microneedles into the target tissue site.

FIG. 14 is a cross-sectional view of a delivery device 220 which has multiple shafts 222 that penetrate the ear to secure the delivery system 224, which releases agent into the tissue of the ear via multiple microneedles 226a, 226b, 226c, such as the barbed shafts shown in the figure. FIG. 14 is a semi cross-sectional view of a delivery device which has two or more shafts that penetrate the ear to secure the device. A series of agent loaded or coated microneedles are attached to a central plunger 224 that passes through a back plate. A shoulder on the back of the plunger retains a spring which is held in a compressed position by a resorbable polymeric coating during administration and for a programmed time period at which time, when the polymeric coating fractures and frees the spring, allows the plunger 224 to rapidly advance and engage the microneedles into the target tissue site.

Example 11: Means for Varying Release Rate, Time, Agent

Figure 15A:
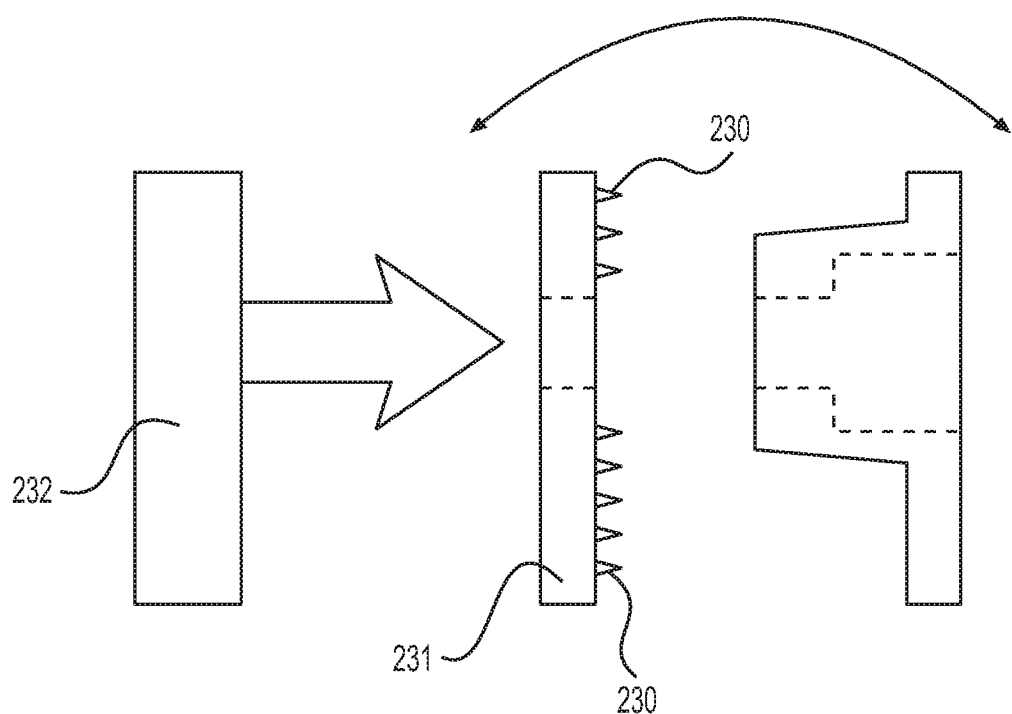
FIGS. 15A and 15B are schematics of the ear tag where the microneedles have more than one height (FIG. 15A in cross-sectional view.

As shown in FIG. 15A, one or more microneedles 230, each in fluid communication with the reservoir 231, extend perpendicularly or in oblique orientation from the reservoir base 232 so that when in the deployed-implanted position, the microneedles 230 will pierce the stratum corneum and protrude into the viable epidermis and/or dermis, in fluid communication between the reservoir 231 contents and the tissue target. Reservoir content conveyance mechanisms to the tissue target include, but are not limited to, osmotic pump system, diffusion rate limiting membranes positioned between the reservoir and the microneedle orifices, and mechanical pump systems.

Figure 15B:
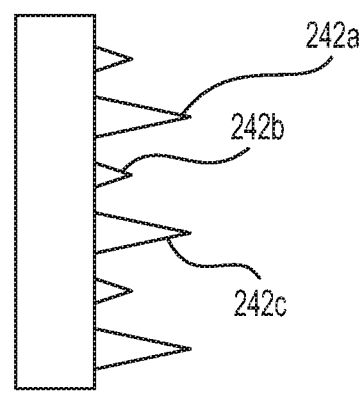

FIG. 15B is a schematic of the ear tag where the microneedles 242 have more than one height, to provide delivery of agent to different depth regions of the ear. This embodiment is applicable to all of the devices described herein.

FIG. 16 is a schematic of the ear tag where there are areas 244, 246, 248 of microneedles for release at different times, such as t=0 (246), t=45 days (247), and t=45 days or other (248).

FIG. 16 also shows a schematic of the ear tag where there are multiple posts, each which can be loaded or coated with a combination polymer and or agent and each with a unique programmed release rate or time point, such as t=0 and t=45 days.

FIGS. 17A and 17B are schematics of a variant of the embodiment of the ear tags of FIGS. 15 and 16, where the microneedle support plate 244 has regions 248a, 248b of microneedles for different release (FIG. 17A) or different microneedles 250a, 250b for different release (FIG. 17B). FIGS. 17A and 17B are schematics of an ear tag where the microneedle arrays are designed to engage the tissue target as isolated and elevated geometries (FIG. 17C) that prevent the entire horizontal base from engaging with the tissue. The base may have perforated or otherwise porous patterned sections so that the ear tissue that is not engaged with the microneedles is in direct contact with light and air as shown in FIG. 17A. FIG. 17B has raised microneedles but the base shown in FIG. 17C is not an open architecture as shown is FIG. 17A. Instead it provides adequate ventilation channels to allow free movement of air around the microneedles and adjacent tissue. This embodiment is particularly useful to avoid pressure necrosis, especially on large surface area microneedle arrays.

Example 12: Delivery Ear Tags where Post is Depot for Agent

Figure 18A:
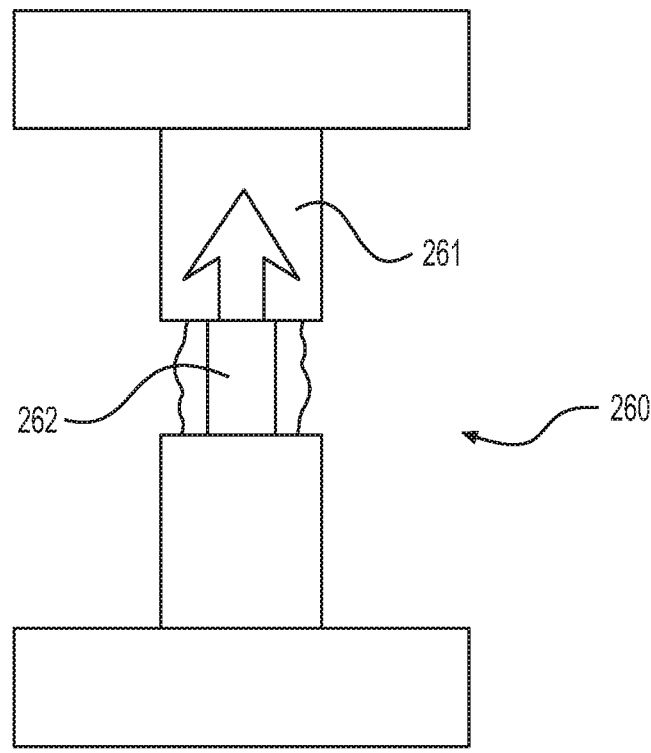
FIGS. 18A and 18B are schematics of an ear tag where there is a matrix of polymer and agent or a coating on the post (FIG. 18A), shown in an expanded view (FIG. 18B), which releases agent(s) perpendicularly to the post and into the exposed inner tissue when it penetrates the ear.
Figure 18B:
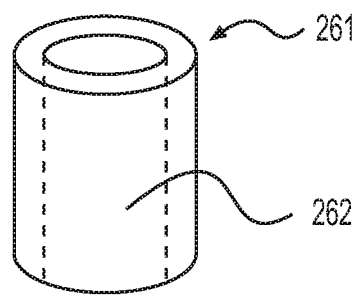

FIGS. 18A and 18B are schematics of an ear tag 260 where there is a depot 262 of agent in the shaft 261 (FIG. 18A), shown in an expanded view 261 (FIG. 18B), which releases agent into the epidermis and dermis when it penetrates the ear.

B. Agents to be Delivered

Agents to be delivered include therapeutic, prophylactic and diagnostic/identifying agents.

Therapeutic agents include antibiotics, anti-helminthes, and antiinfectives (antiviral, antibiotic, antifungal).

Representative vaccines include the antigens for BRD, Infectious Bovine Rhinotracheitis (IBR), Bovine Virus Diarrhea Types 1 and 2 (BVD), Parainfluenza 3 (PI3), Bovine Respiratory Syncytial Virus (BRSV) *Vibrio cholerae* (*Vibrio*), 5 Strains of Leptospirosis Bacteria (Lepto), Harjo-Bovis, *Haemophilus somnus*, Clostridial bacteria including *Chauvoei, Septicum, Novyi, Sordelli, Perfringens* Types C&D, and *Haemolyticum*. Vaccines for diarrhea and Pneumonia include inactivated bovine rotavirus (serotypes G6 and G10) and coronavirus. K99 *E. colibacterin*, and *Clostridia perfringens* type C and/or D. Vaccines may include adjuvant. The vaccine is adjuvanted to enhance the immune response.

Representative antibiotics include tulathromycin, a macrolide antibiotic used to treat bovine respiratory disease in cattle and swine respiratory disease in pigs, tylosin, an antibiotic and a bacteriostatic feed additive used in veterinary medicine with a broad spectrum of activity against Gram-positive organisms and a limited range of Gram-negative organisms, enrofloxacin, a fluoroquinolone antibiotic, cephalosporins, florfenicol, a fluorinated synthetic analog of thiamphenicol, mainly used in veterinary medicine, tetracylines like oxytetracycline and penicillins. Classes of antibiotics of veterinary importance include aminoglycosides, beta-lactam antibiotics, chloramphenicol, fluoroquinolones, glycopeptides, lincosamides, polymixins, and macrolides.

Diagnostic or identifying agents include dyes that can create a tattoo, magnetic particles and microchips. For example, the dyes may imprint the date and what is administered, providing a permanent record for source verification.

Nutraceuticals can include, but are not limited to, trace minerals such as selenium, vitamins such as vitamins E and A, iron, chromium, cobalt, zinc, manganese, and copper.

C. Labelling

The tags may be labelled with identification numbers and/or letters, or a farm/ranch name, or combination thereof. The tags may also be labelled to identify agents administered.

D. Optional Electronic Circuitry

Integration of diagnostic, therapeutic and or communicative electronics provides a key platform for assimilation to and capitalization of blockchain technology.

The tags may include electronic identification circuitry, sensors for physiologic monitoring such as body temperature, heart rate and respiration rate, sensors for external environmental conditions such as temperature, humidity and methane levels. Tags can contain GIS technology. Tags may contain solar collection arrays and storage, systems used to energize, for example, electronic and sensing components. Integration of diagnostic, therapeutic and/or communicative electronics.

II. Methods of Making

Figure 19A:
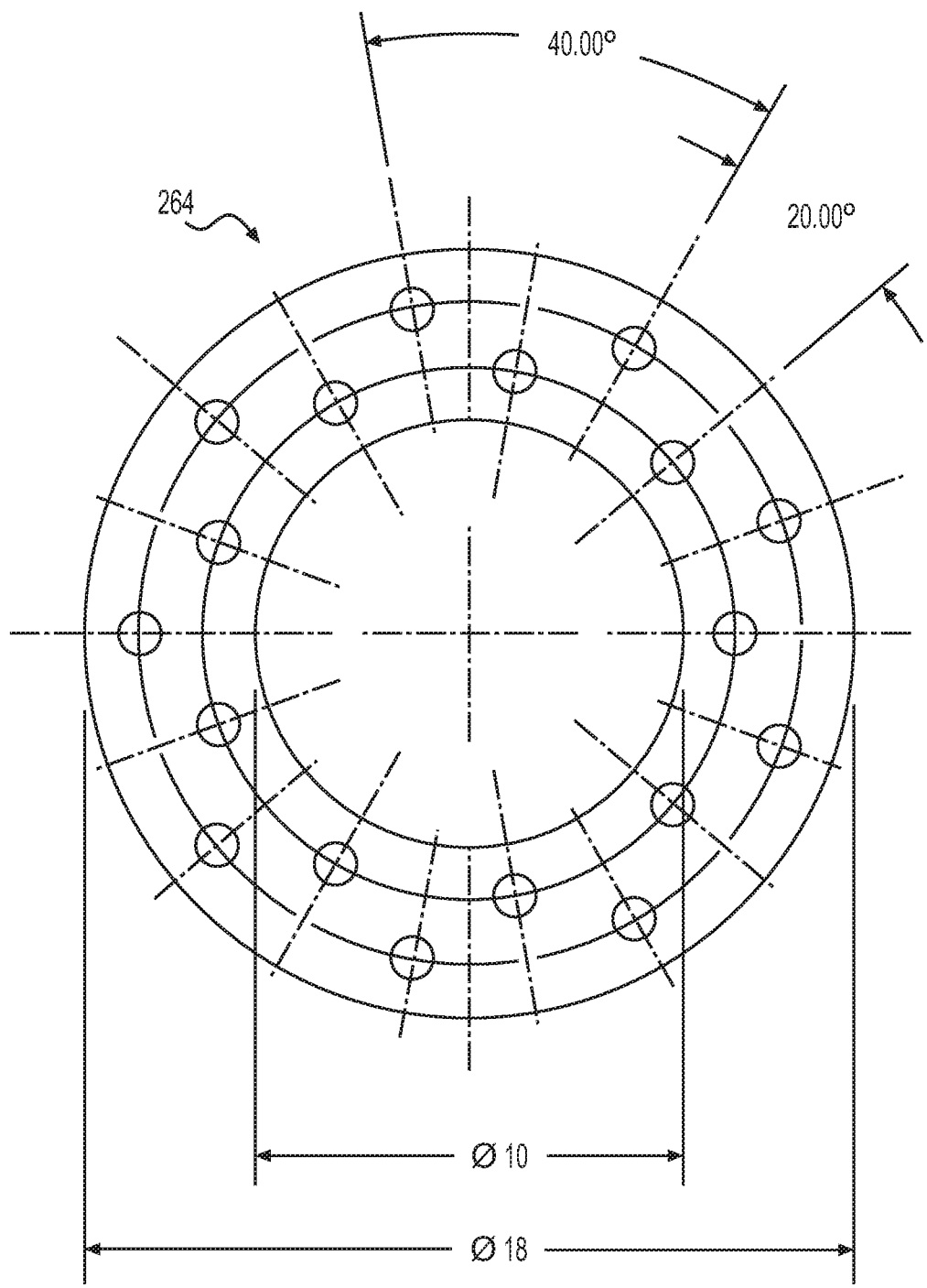
FIGS. 19A and 19B are schematics of a mold to make a microneedle array (FIG. 19A perspective view.
Figure 19B:
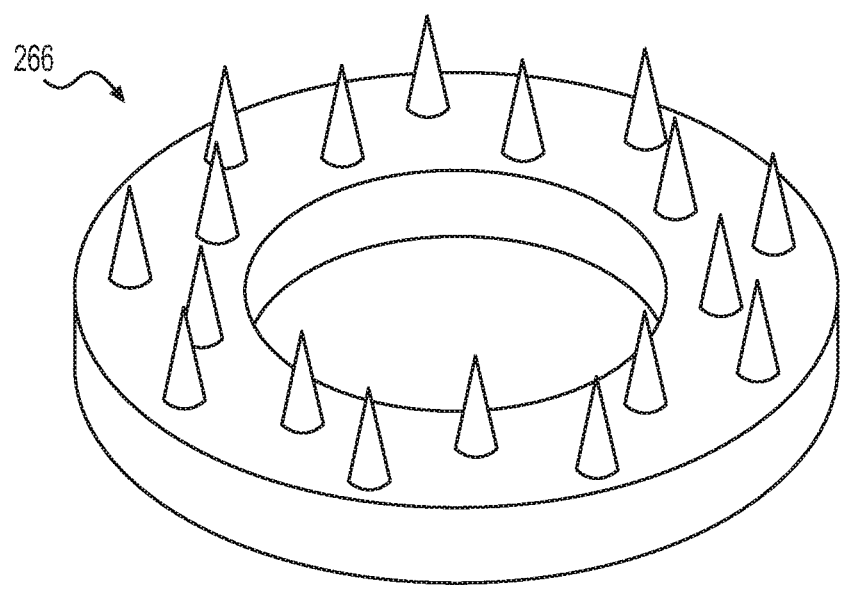

The support base, shaft, receiver and other pieces are created by techniques such as extrusion, molding or die cutting. The microneedles are made using standard techniques for manufacture of microneedles, such as micromolding (see, for example, Nejad, et al., Microsystems & Nanoengineering 4:17073 (2019)) or photolithography (Park, et al. Journal of Controlled Release. 104 (1): 51-66 (2005)). These methods involve etching microscopic structure into resin or silicon in order to cast microneedles, as shown in FIGS. 19A and 19B. FIGS. 19A and 19B are schematics of a mold 264 to make a microneedle insert 266. In one embodiment, antigen or other drug is mixed with PVP in a w/w ratio such as 200 with 1-vinyl-2-pyrrolidinone (PVP) monomer and/or polymer in water with photoinitiator such as IRACURE 2959 2-Hydroxy-4'-(2-Hydroxyethoxy)-z-methylpropriophenone added to monomer at a 0.5-1.0 w/w percent concentration, which is then poured into the mold and crosslinked to form the microneedles. Other preferred polymers include sorbitol and alginate. The microneedle therapeutic arrays may be manufactured by three dimensional printing with, for example, polymer and or metallic materials. They may be produced by micro-molding and or micro-machining techniques common and known to those skilled in the art. They may be solvent cast.

Microneedles are made from a variety of material including silicon, titanium, stainless steel, and polymers, or the agent to be delivered, or combination thereof. Therapeutic delivery system platform tags may be made from degradable or non-degradable materials or with a combination of both. For example, the male member shaft may be manufactured with a degradable material programmed by design to degrade after the therapeutic utility if the device if expired. In this example, after the device has completed its mission, the male member would degrade and allow the device to self-detach. Complete biodegradation may also be desired for environmental reasons. Examples of useful degradable materials include, but are not limited to, poly(L-lactide), poly(caprolactone), poly(lactide co-glycolide), poly(glycolic acid), poly(anhydrides), poly(hydroxybutyrate-co valerate), starches, sugars, and sodium carboxymethyl cellulose. Microneedle therapeutic array materials may also be or include, poly(vinylpyrrolidone), poly(ethylene-glycol), poly(methylmethacrylate), and silicon.

Microneedle therapeutic arrays may be made solely with an active pharmaceutical ingredient (API) with or without a polymeric substrate or matrix support. API's may be formulated with excipients like carboxymethyl cellulose, alginate, chitosan, sodium lauryl sulfate, lactic acid, albumin, phosphorylcholine, soy polysaccharides, poly(vinylpyrrolidone) or poly(ethylene-glycol) all of which act as a vehicle or medium for a drug or other active substance. Immune response may be enhanced with adjuvants such as Alum, an aluminum salt, AS04, an adjuvant that is a combination of alum and monophosphoryl lipid A (MPL), an immune-stimulating lipid (fat).

The pieces can be attached by thermal means such as, but not limited to, inductive heating, welding or molding, adhesive means such as, but not limited to, cyanoacrylates, epoxies and UV cured materials, locking, or other physical attachment methods such as, but not limited to, locking undercuts, screws, pins and clips.

Microneedles are sized as appropriate for the animal, the thickness of its skin, the agent to be delivered, and the time of release(s). Microneedles will typically be up to 1000 µm in height with a base diameter of 400-1000 µm, aspect ratio ranges of 1:3-1:5 and a volume of $4.2 \times 10^2$ mm$^3$ in an array of 266 microneedles for a total array volume of 11.142 mm$^3$. An array may be include combinations of microneedle sizes and volumes. For example, one therapeutic member may have an array of 400 µm×1000 µm microneedles and another may have an array of 200 µm×500 µm microneedles. The former is designed to penetrate into the outer viable epidermis skin layer and the latter is designed to penetrate the stratus corneum and into the inner viable epidermis, each with a specific targeted therapeutic endpoint. An individual therapeutic member may have more than one, variable sized microneedle within a single array.

Microneedle therapeutic arrays may be made in multiple layers which allows for multiple therapeutic substances to be integrated into a single microneedle array. Each layer may be separated by a rate controlling membrane such as, but not limited to, poly(epsilon caprolactone).

For example, the microneedle array could be formed of a PVP/Alginate with an API (active pharmaceutical agent) core insulated by a PLGA layer which is covered by another PVP/Alginate API layer. This outermost formulation would release quickly upon deployment contact with skin, in particular, after penetration through the stratum corneum and into the viable epidermis. The PLGA layer would then be exposed to tissue and interstitial fluids which would activate degradation of the protective membrane at a rate designed to reach completion in a time window within which the initiation of the secondary booster dose is programmed to begin, for example at 45 days post t=0.

The device weight range will typically be between 150 and 750 mg.

Coatings can have thicknesses of between 6.25 and 800 µm. The microneedles are preferably coated with a release rate controlling material such as polylactide acid. Other materials can be used with or in place of the PLGA coatings. For example, pH sensitive release controlling materials include fatty acids such as Lauric acid, palmitic acid, stearic acid, and myristic acid. Lauric acid provides a pH sensitive degradation trigger. Calcium carbonate may be used to reduce the local acidity created from PLGA or other linear aliphatic polyester degradation.

Rather than coating the microneedles, microparticles can be manufactured using the same or other materials and coated them with the degradation control coating (e.g., PLGA) and included within the microneedles. As with the microneedles coating, different degradation rates can be controlled by the coating thickness as well as composition. Multiple antigens can be encapsulated separately from one another and loaded into the microneedles. This separates microneedles mechanical performance from active delivery. Soon after deployment the microneedles dissolve and the API loaded microparticles are released. These remain intact for a period of time, depending on their programmed degradation time.

Loading ranges are typically between 10 and 1000 µg/array. Increased loading can be accommodated by increasing needle volume and or quantity.

Figure 20B:
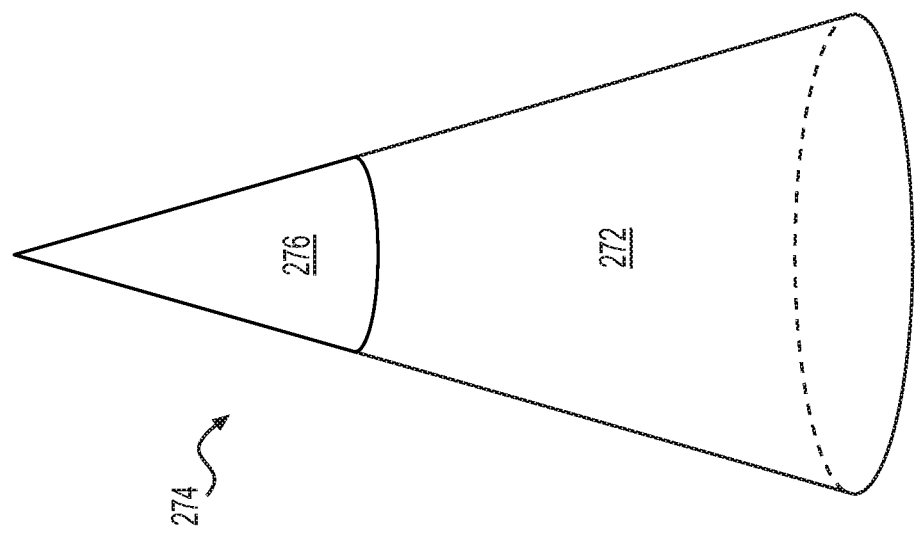
FIGS. 20A and 20B are schematics of microneedles that can be made, with agent to be delivered dispersed, either as particles of the agent or particles of the agent in a matrix of a polymer or other inert matrix, throughout the microneedle (FIG. 20A) and with a solid tip to increase the ability of the microneedle to penetrate tissues (FIG. 20B).
Figure 20A:
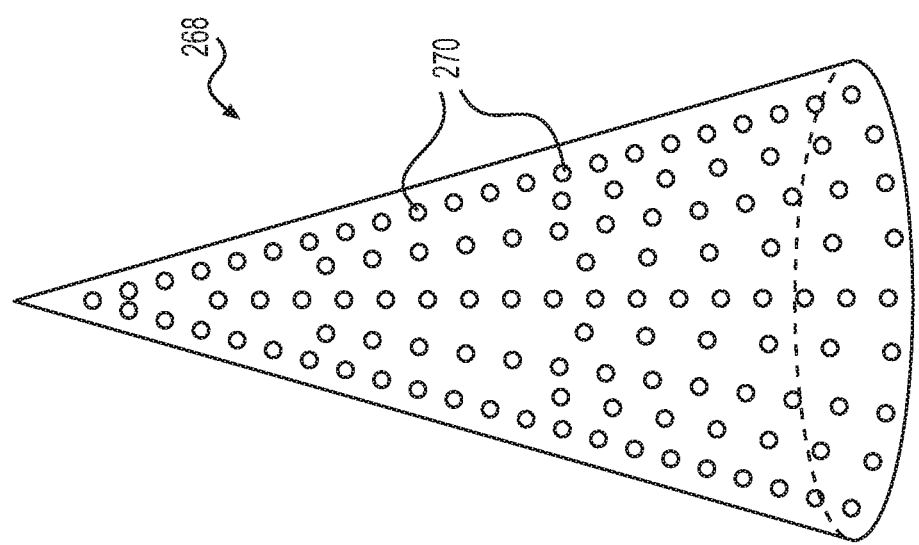

FIGS. 20A and 20B are schematics of microneedles 268, 270 that can be made, with agent 270 to be delivered dispersed, either as particles of the agent or particles of the agent in a matrix 272 of a polymer or other inert matrix, throughout the microneedle 268 (FIG. 20A) and with a solid tip 274 to increase the ability of the microneedle to penetrate tissues (FIG. 20B). These can be made using the micromolds shown in FIGS. 19A and 19B, having the same or different dimensions, with a uniform composition or with a different composition in the tip 276, for example, as shown in FIG. 20B, which may be stronger for penetration into the skin, or breakable so that the agent to be delivered penetrates into the dermis, and then breaks off from the microneedles bound to the substrate.

III. Methods of Using

Tags may be placed in one or both ears and more than one tag may be placed in each ear. Tags are applied to animals in need of therapeutic or prophylactic treatment, (such as with vaccines), typically using a clamping device, which will have clots, clamps, springs, or other means of securing the male member of the tag device in one arm of the device and another means of securing the female member of the tag device in the other arm of the device, so that the clamping device can be positioned on either side of the animal's ear, and the tag device secured by clamping the two arms together until the one or more shafts penetrate the ear and secure the delivery means in juxtaposition with the skin, preferably at a site with less hair.

There are a number of commercially available applicators that can be used to position the tag. ALLFLEX makes a universal tag applicator, which includes a bracket to secure the female member on one arm and a pin to insert into the shaft of the male member so that when the handles are compressed, the male member penetrates the ear and engages into the female member.

As part of a strategic program that consistently supports animal health, a single administration, multi-dose vaccine delivery system will provide timely protective immunity and decrease stress by eliminating booster processing and thereby improving an animal's response to downstream stresses. Along with well-implemented management practices, this technology supports animal health and helps address the growing problem of antibiotic resistance. Such a strategy will help animals adapt and transition to challenging environments with less morbidity and mortality. One example where this technology will play an important role is in the prevention of bovine respiratory disease (BRD), one of the leading causes of death in cattle. For example, stressed calves are especially vulnerable to BRD infection. Contributors to stress are separation and handling, dietary changes, variations in weather, transportation, animal mixing, poor environment, castration, dehorning and stocking density. Single administration, single intervention pre-weaning vaccine delivery can greatly improve calf health and help ensure calf durability in this important developmental timeframe.

As a result, this technology platform can reduce the cost of gain and increase the value of gain. Post scale-up COGS are expected to support and be competitive with current pricing structures, which is extremely important, especially for smallholders in developing nations. Importantly, this technology has great potential to benefit livestock and livestock producers in all world economies, including and perhaps especially in developing countries.

These devices should help producers meet prescribed dose compliance (single administration: primary and booster doses per manufacturer's specification without a secondary intervention which results in improved level of protective immunity), reduced stress on calves and mothers (improved health), safety of calf and administrator (enhanced via mode of application and reduced handling), simplify logistics (e.g., option to leave cattle on grass longer, no delayed turnout or early gather to administer the "booster", thereby providing management flexibility to fit needs of operator and herd).

We claim:

1. An ear tag delivery device for use with an ear tag device that is secured in an ear of an animal, the ear tag delivery device comprising
 a first structure configured to penetrate the ear and deliver of one or more therapeutic, prophylactic, diagnostic or identifying agent contained therein to the ear of the animal, and
 a second structure forming a base for the first structure, wherein the second structure is configured to juxtapose the first structure to the epidermis and global dermis of the ear when secured to the ear tag device to ensure penetration of the agent from the first structure into the dermis.

2. The ear tag delivery device of claim 1 wherein the agent for delivery is selected from the group consisting of antiinfectives, trace elements, probiotics and vaccines.

3. The ear tag delivery device of claim 1 wherein the second structure comprises one or more structures selected from the group consisting of microneedles, macroneedles, elastomeric membranes, and hydrogels.

4. The ear tag delivery device of claim 1 wherein the ear tag device is secured in the ear by one or more posts configured for penetrating through the ear.

5. The ear tag delivery device of claim 1 wherein the ear tag device comprises a male member with a receiving shaft and a tip configured for penetrating through the ear into a shaft of a female member on the ear tag device which secures the ear tag device in abutment with both sides of the ear, wherein the ear tag delivery device is placed in abutment with the male member prior to penetration of the shaft and tip through the ear and into the female member.

6. The ear tag delivery device of claim 1 further comprising a reservoir for the agent to be delivered.

7. The ear tag delivery device of claim 1 wherein the first structure comprises microneedles which penetrate into the dermis of the ear when the base is secured in abutment to the ear.

8. The ear tag delivery device of claim 7 wherein the microneedles have agent dispersed therein, thereon or are formed of the agent to be delivered, and/or have a coating to regulate release of the agent.

9. The ear tag delivery device of claim 1 wherein the first structure for delivering agent provides continuous, pulsed and/or delayed release of the agent.

10. The ear tag delivery device of claim 1 wherein the second structure of the ear tag delivery device is positioned near an edge of the ear.

11. The ear tag delivery device of claim 1 wherein the second structure of the ear tag delivery device comprises a spring contacting the first structure for delivery of agent and configured to move the first structure for delivering agent towards the ear, thereby facilitating penetration of agent either from an elastomeric membrane or a hydrogel and/or microneedles into the dermis of the ear.

12. The ear tag delivery device of claim 1 wherein the first structure comprises a trigger to facilitate positioning of the second structure for delivering agent into the ear.

13. The ear tag delivery device of claim 1 wherein the first structure comprises microneedles of different dimensions, effecting release of the agent at different times and/or penetrating into different parts of the dermis.

14. The ear tag delivery device of claim 1 wherein the second structure comprises channels or pores to avoid pressure necrosis and/or to increase access of air to the skin.

15. The ear tag delivery device of claim 1 wherein the first structure of the ear tag delivery device is positioned on or within a shaft that penetrates the ear to secure a male member of the ear tag device to a female member of the ear tag device, wherein the second structure of the ear tag delivery device is an elastomeric membrane or a hydrogel, microneedles which are barbed, or a reservoir in the shaft of the ear tag device.

16. A method of making the ear tag delivery device of claim 1 comprising
 providing a first structure configured to penetrate the ear and deliver one or more therapeutic, prophylactic, diagnostic or identifying agents to the ear of an animal, and
 providing a second structure forming a base for the first structure,
 wherein the second structure is in contact with the first structure for delivery of agent,
 wherein the second structure is configured to juxtapose the first structure to the epidermis and global dermis of the ear when the second structure is secured to an ear tag device to penetration of the agent from the first structure into the dermis,
 wherein the first structure is selected from the group consisting of microneedles or an elastomeric membrane or hydrogel on a support structure, and the first or second structure having thereon or therein therapeutic, prophylactic and/or diagnostic or identification agent for ensure administration to the ear of a livestock or a domestic pet animal.

17. The method of claim 16 wherein the second structure for delivery of agent is a plurality of microneedles having the agent incorporated therein or thereon.

18. The method of claim 17 comprising forming the microneedles by micromolding, from the agent or a mixture of agent and excipient, and further applying a release controlling coating on the microneedles.

19. The method of claim 16 comprising providing a reservoir in the first or second structure of the ear tag delivery device in combination with an elastomeric membrane or a hydrogel as the first structure for delivery of agent.

20. A method of applying the ear tag delivery device of claim 1 comprising placing the ear tag delivery device in abutment with either of a male member of the ear tag device in one arm of a clamping device or a female member of the ear tag device in a second arm of the clamping device, placing the arms on opposite sides of an animal's ear, with the first structure of the ear tag delivery device in juxtaposition with the animal's ear, and compressing the first and second arms of the clamping device to secure the male and female members of the ear tag device to each other, with the first structure for delivery of agent in secure contact with the skin of the animal's ear.

21. A kit comprising the ear tag device of claim 1, an ear tag device and a clamping device for application to an animal's ear.

* * * * *